United States Patent
Insel et al.

(10) Patent No.: US 12,138,286 B2
(45) Date of Patent: Nov. 12, 2024

(54) COMBINATION METHOD FOR TREATING OR PREVENTING CHILDHOOD ATOPIC DISEASE

(71) Applicant: Johnson & Johnson Consumer Inc., Skillman, NJ (US)

(72) Inventors: Richard A. Insel, Skillman, NJ (US); Linda Alunkal, Wayne, PA (US); Russell Gould, Skillman, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 18/519,981

(22) Filed: Nov. 27, 2023

(65) Prior Publication Data
US 2024/0165172 A1 May 23, 2024

Related U.S. Application Data

(63) Continuation of application No. PCT/IB2023/055593, filed on May 31, 2023.

(60) Provisional application No. 63/347,206, filed on May 31, 2022.

(51) Int. Cl.
| | |
|---|---|
| *A61K 35/745* | (2015.01) |
| *A61K 9/00* | (2006.01) |
| *A61K 31/164* | (2006.01) |
| *A61K 35/00* | (2006.01) |
| *A61P 17/00* | (2006.01) |

(52) U.S. Cl.
CPC .......... *A61K 35/745* (2013.01); *A61K 9/0014* (2013.01); *A61K 9/0053* (2013.01); *A61K 31/164* (2013.01); *A61P 17/00* (2018.01); *A61K 2035/115* (2013.01)

(58) Field of Classification Search
None
See application file for complete search history.

(56) References Cited

U.S. PATENT DOCUMENTS

| | | | |
|---|---|---|---|
| 11,173,113 B2 | 11/2021 | Leitner et al. | |
| 2020/0306368 A1* | 10/2020 | Nadeau | A61K 35/747 |
| 2021/0361723 A1 | 11/2021 | Jeon | |
| 2023/0309921 A1 | 10/2023 | Oddos et al. | |

FOREIGN PATENT DOCUMENTS

| | | |
|---|---|---|
| KR | 20040068820 A | 8/2004 |
| KR | 20050062495 A | 6/2005 |
| WO | 2016149687 A1 | 9/2016 |
| WO | 2017060468 A1 | 4/2017 |
| WO | 2022-112927 A1 | 6/2022 |

OTHER PUBLICATIONS

Clinical Trial NCT04662619 (https://clinicaltrials.gov/study/NCT04662619?id=nct04662619&rank=1&a=2&tab=history; Dec. 18, 2020).*
Hourihane et al (Early initiation of short-term emollient use for the prevention of atopic dermatitis in high risk infants—the STOP AD randomised controlled trial. Authorea. Apr. 8, 2022 DOI: 10.22541/au.164940311.12725370/v1).*
Skjerven et al., "Skin emollient and early complementary feeding to prevent infant atopic dermatitis (PreventADALL): a factorial, multicentre, cluster radomised trail," Lancet Lond. Engl., 2020, 395, 10228: 951-961.
Lowe et al. "A randomized trial of a barrier lipid replacement strategy for the prevention of atopic dermatitis and allergic sensitization: the PEBBLES pilot study," Br. J. Dermatol., 2018, 178(1):e19-e21.
Mindell et al., Norm-referenced scoring system for the Brief Infant Sleep Questionnaire—Revised (BISQ-R). Sleep Med 2019;63:106-14.
Turroni, et al., "Glycan Utilization and Cross-Feeding Activities by Bifidobacteria" Trends in Microbiology, 2018, vol. 26 (4): 339-350.
Masi et al., "Untangling human milk oligosaccharides and infant gut microbiome", iScience 25, 103542, Jan. 21, 2022, 1-15.
Abrams et al., "International Peanut Allergy prevention, 6 Years After the Learning Early About Peanut Study," J. Allergy Clin. Immunol Pract., Jan. 2022, vol. 10 (1): 71-77.
Akay et al., "The relationship between bifidobacteria and allergic asthma and/or allergic dermatitis: A prospective study of 0-3 years-old children in Turkey", Anaerobe 28, 2014, 98-103.
Akdis, "The epithelial barrier hypothesis proposes a comprehensive understanding of the origins of allergic and other chronic noncommunicable diseases", J. Allergy Clin. Immunol., 2022, vol. 149 (1): 41-44.
Akdis, "Does the epithelial barrier hypothesis explain the increase in allergy, autoimmunity and other chronic conditions?", Nature Reviews Immunology, 2021 (21): 739-751.
Benninga et al., "Childhood functional gastrointestinal disorders: neonate/toddler", Gastroenterology 2016;150:1443-55.
Chalmers et al, "Daily emollient during infancy for prevention of eczema: the BEEP randomised controlled trial," Lancet Lond. Engl., 2020, 395 (10228):962-972.
Chaoimh et al., "Early initiation of short-term emollient use for the prevention of atopic dermatitis in high-risk infants—The STOP-AD randomised controlled trial", 2022, 984-994.
Charman et al., The Patient-Oriented Eczema Measure: Development and initialvalidation of a new tool for measuring atopic eczema severity from the patients perspective. Arch Dermatol 2004;140:1513-1519.
Charman et al., Translating Patient-Oriented Eczema Measure (POEM) scores into clinical practice by suggesting severity strata derived using anchor-based methods. Br J Dermatol 2013, 169:1326-32.
Clinical Trials, NCT03871998, "Short-term Topical Application to Prevent Atopic Dermatitis (STOP AD)", First posted Mar. 12, 2019, pp. 1-18.

(Continued)

*Primary Examiner* — Brian Gangle
(74) *Attorney, Agent, or Firm* — BakerHostetler

(57) ABSTRACT

The present application describes methods of treating or reducing the onset or occurrence of childhood atopic disease. In particular, it relates to an integrated solution that accounts for temporal and sequential administrations of three different and specific approaches for optimal effectiveness in treating or reducing the onset or occurrence of childhood atopic disease.

20 Claims, No Drawings

(56) References Cited

OTHER PUBLICATIONS

Clinical Trials, NCT04662619, A Study of a Probiotic Food Supplement Containing B. Infantis (EVC001) in Healthy Breastfed Infants at Rish of Developing Atopic Dermatitis, First posted Dec. 10, 2020, pp. 1-13.

Du Toit, George et al., "Randomized Trial of Peanut Consumption in Infants at Risk for Peanut Allergy," N. Engl. J. Med., Feb. 2015, vol. 372 (9): 803-813.

Ganemo et al., Usefulness of Rajka and Langeland Eczema Severity Score in clinical practice:, Acta Derm Venereol 2016;96:521-524.

Hanifin et al., "The eczema area and severity index (EASI): assessment of reliability in atopic dermatitis", EASI Evaluator Group, Exp Dermatol 2001;10:11-18.

Kanwar et al., Book Reviews, Indian J Med Res. Jan. 2018; 147(1): 117-118.

Mayurkumar et al., Fingolimod hydrochloride gel shows promising therapeutic effects in a mouse model of atopic dermatitis, JPP, 2016, 1268-1277.

McClanahan et al., "A randomized controlled trial of an emollient with ceramide and filaggrin-associated amino acids for the primary prevention of atopic dermatitis in high-risk infants," J. Eur. Acad. Dermatol. Venereol., 2019, 33 (11):2087-2094.

Moncrieff et al., Cost and effectiveness of prescribing emollient therapy for atopic eczema in UK primary care in children and adults: a large retrospective analysis of the Clinical Practice Research Datalink, BMC Dermatology, 2018, 18:9, pp. 1-11.

Perkin et al., "Randomized Trial of Introduction of Allergenic Foods in Breast-Fed Infants," N. Engl. J. Med., 2016, 374: 1733-1743.

Rajka et al., "Grading of the severity of atopic dermatitis", Acta Derm Venereol Suppl (Stockh) 1989;144:13-14.

Smilowitz et al., "Safety and tolerability of Bifidobacterium longum subspecies *infantis* EVC001 supplementation in healthy term breastfed infants: a phase clinical trial", BMC Peadiatrics, 2017, 17:133, pp. 1-11.

Zeevenhooven et al., "The new Rome IV criteria for functional gastrointestinal disorders in infants and toddlers", Pediatr Gastroenterol Hepatol Nutr 2017;20:1-13.

\* cited by examiner

COMBINATION METHOD FOR TREATING OR PREVENTING CHILDHOOD ATOPIC DISEASE

CROSS-REFERENCE TO RELATED APPLICATIONS

This application is a continuation of PCT/IB2023/055593, filed May 31, 2023, which claims the benefit of U.S. provisional patent application 63/347,206, filed May 31, 2022, the contents of each are incorporated by reference in their entirety.

FIELD OF THE APPLICATION

This application describes combinations and methods of using the combinations for treating or reducing the onset or occurrence of childhood atopic disease. In particular, it relates to an integrated solution that accounts for temporal and sequential administrations of three different approaches for optimal effectiveness in treating or reducing the onset or occurrence of childhood atopic disease.

BACKGROUND OF THE INVENTION

The prevalence of pediatric allergic disease, also known as childhood atopic disease, is increasing globally. An estimated 20% of children suffer from eczema (atopic dermatitis), and 8% of children report an allergy to at least one food. Atopic disease represents a failure of immune tolerance and a subsequent overreaction to benign inhalant (environmental) or food allergens. While there is substantial research into the potential genetic, metabolomic, environmental, and socioeconomic predictive correlates of atopic disease, current clinical guidance for allergic disease focuses on avoidance of allergens and acute treatment of exacerbations and not on prevention.

Prevention of childhood atopic disease requires a multimodal approach that addresses several root causes that result in immune system dysregulation and failure of establishment or maintenance of immune tolerance. In early infancy, a disordered skin barrier either in the presence or absence of eczema and an altered skin microbiome enables food and inhalant allergens to sensitize the infant with generation of immune cells that migrate to the gut or lung to lead to food allergy or asthma, respectively. Additionally, infants born today in the modernized world lack important keystone gut microbes and thus their functionality arising from antibiotic exposure, C-section delivery, lack of breastfeeding, and/or trans-generation effects of their mothers exposed to the same insults. This gut dysbiotic microbiome fails to induce a tolerogenic state and results in a pro-inflammatory environment that mis-characterizes benign antigens. Finally, erroneous historical medical advice and parental anxiety results in a delay of food introduction in infancy that is required for optimal immune training to specific foods.

While individual solutions, e.g., moisturizers and emollients, probiotics, and food introduction products, have been developed and are marketed to concerned parents, there has not been development of an easy to use, parent administered, integrated solution that accounts for the specific temporal and sequential administration requirements necessary for optimal effectiveness in prevention of childhood allergic disease. Therefore, there exists a need for the development of such solutions to prevent childhood atopic disease, such as atopic dermatitis or eczema, food allergy and asthma.

SUMMARY OF THE INVENTION

This application describes methods of treating or reducing the onset or occurrence of childhood atopic disease. In particular, this application describes methods that integrate individual solutions, such as, eczema moisturizers and emollients, probiotics, and food introduction products, in a temporal manner.

In one general aspect, this application describes a method of treating or reducing the onset or occurrence of childhood atopic disease, such as atopic dermatitis, in a subject in need thereof, the method comprising conducting at least two of:

(a) topically administering to a skin area of the subject a first composition, wherein the first composition comprises a skin barrier function composition, and administration of the first composition starts from within about seven days, more particularly within about six days, five days, four days, three days, two days or one day, after birth of the subject and continues to at least about two months after birth of the subject;

(b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food; and (c) orally administering to the subject premeasured doses of one or more food allergens, wherein the administration of the one or more food allergens starts within about 1-8 months, more particularly within about 2-6 months, after the birth of the subject.

In another general aspect, this application describes a first composition for use in a method of treating or reducing the onset or occurrence of childhood atopic disease, such as atopic dermatitis, in a subject in need thereof, the method comprising conducting at least two of:

(a) topically administering to a skin area of the subject the first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;

(b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food; and (c) orally administering to the subject premeasured doses of one or more food allergens, wherein the administration of the one or more food allergens starts within about 1-8 months, more particularly within about 2-6 months, after the birth of the subject.

In another general aspect, this application describes a second composition comprising an effective amount of a probiotic, such as a *Bifidobacterium* cell, for use in a method of treating or reducing the onset or occurrence of childhood atopic disease, such as atopic dermatitis, in a subject in need thereof, the method comprising conducting at least two of:

(a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;

(b) orally administering to the subject the second composition, wherein the administration of the second composition starts from within about 30 days, more particularly within about 28 days, 21 days, 14 days, or 7 days, after the birth of the subject and optionally continues to at least prior to introduction of solid food; and (c) orally administering to the subject premeasured doses of one or more food allergens, wherein the administration of the one or more food allergens starts within about 1-8 months, more particularly within about 2-6 months, after the birth of the subject.

In another general aspect, this application describes premeasured doses of one or more food allergens for use in a method of treating or reducing the onset or occurrence of childhood atopic disease, such as atopic dermatitis, in a subject in need thereof, the method comprising conducting at least two of:

(a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;

(b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food; and (c) orally administering to the subject the premeasured doses of one or more food allergens, wherein the administration of the one or more food allergens starts within about 1-8 months, more particularly within about 2-6 months, after the birth of the subject.

In some embodiments, the method comprises conducting (a) and (b), preferably the administration of the first composition starts before the administration of the second composition.

In some embodiments, the method comprises conducting (a) and (c).

In some embodiments, the method comprises conducting (b) and (c).

In some embodiments, the method comprises conducting (a), (b) and (c), preferably the administration of the first composition starts before the administration of the second composition.

In some embodiments, the first composition comprises an emollient, more particularly the first composition further comprises colloidal oatmeal, ceramides, and distearyldimonium chloride.

In some embodiments, the administration of the second composition continues until a desired gut microbiota is established.

In some embodiments, the subject receives one, two, three, four, five or more administrations of the second composition.

In some embodiments, the administration of the second composition continues at least for 12 weeks.

In some embodiments, the probiotic comprises a bacterial strain selected from *Lactobacillus*, *Lacticaseibacillus* and *Bifidobacterium* genera, more particularly comprises *Bifidobacterium* cell.

In some embodiments, the *Bifidobacterium* cell is a *B. infantis* cell.

In some embodiments, the second composition comprises about 0.1 to about 100, more particularly about 5 to about 15, most particularly 8, billion colony forming units (CFU) of *B. infantis*.

In some embodiments, the administration of the one or more food allergens comprises:

i. administering to the subject a first food allergen at an exposure dose for the first food allergen for one or more days;

ii. subsequently administering to the subject the first food allergen at a maintenance dose for the first food allergen for multiple days;

iii. subsequently administering to the subject the first food allergen at the maintenance dose and a second food allergen at an exposure dose for the second food allergen for one or more days; and iv. subsequently administering both the first and the second food allergens at maintenance doses for each food allergen for multiple days.

In some embodiments, the administration of the one or more food allergens further comprises:

v. administering to the subject a third food allergen at an exposure dose for the third food allergen for one or more days, vi. subsequently administering to the subject the first food allergen, the second food allergen, and the third food allergen at maintenance doses for each of the food allergens for multiple days.

In some embodiments, the method further comprises continuing the maintenance doses of the first food allergen, the second food allergen, and the third food allergen until the premeasured doses for each of the food allergens are consumed.

In some embodiments, the premeasured doses for each of the first, second and third food allergens are consumed over 12 days.

In some embodiments, the first food allergen, second food allergen and third food allergen are each independently selected from the group consisting of cow milk, egg, peanut, wheat, soy, sesame, fish, shellfish, and tree nut, preferably cow milk, egg, and peanut, respectively.

In another general aspect, the application describes a kit or a combination containing at least two of a first composition which is a skin barrier function composition, a second composition comprising an effective amount of a *Bifidobacterium* cell, and premeasured doses of one or more food allergens for use in a method described herein.

Other aspects, features and advantages of the invention will be apparent from the following disclosure, including the detailed description of the invention and its preferred embodiments and the appended claims.

DETAILED DESCRIPTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It is noted that as used herein and in the appended claims, the singular forms "a," "an," and "the" include plural reference unless the context clearly dictates otherwise.

Throughout this specification and the claims which follow, unless the context requires otherwise, the word "comprise", and variations such as "comprises" and "comprising", will be understood to imply the inclusion of at least the one or more listed elements (e.g., stated integer(s), or step(s), etc.) but not the exclusion of other non-listed elements, i.e., other elements that are not mentioned may also be present. When used herein the term "comprising" can be substituted with the term "containing" or "including" or sometimes when used herein with the term "having".

Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The term "between" as used in a phrase as such "between A and B" or "between A-B" refers to a range including both A and B.

As used herein, "essentially free" or "substantially free" of an ingredient means containing less than 0.1 weight percent of the ingredient. In some embodiment, "essentially free" or "substantially free" of an ingredient means containing less than 0.01 weight percent, or none of the ingredient.

As used herein, the terms "method" and "procedure" are used interchangeably.

As used herein, the terms "atopic disease" and "allergic disease" can be used interchangeably. Atopic diseases are a class of diseases in which the immune system develops Immunoglobulin IgE to common environmental allergens which are generally considered to be harmless. Examples of atopic diseases include, but not limited to, atopic dermatitis (AD), allergic rhinitis, asthma, and food allergy.

As used herein, the term "atopic dermatitis" or "eczema" refers to a chronic relapsing inflammatory skin disorder that makes skin itchy and/or red. Pruritus or itchy skin is a primary symptom of atopic dermatitis, which can also have skin lesions ranging from mild erythema to severe lichenification to erythroderma. It is common in children but can occur at any age. Atopic dermatitis may be accompanied by asthma or hay fever. There is currently no cure for atopic dermatitis.

As used herein, the term "subject" refers to a human. In particular, the subject is an infant. More particularly, the subject is an infant at increased risk of developing childhood atopic disease, for example, an infant having one first-degree relative having a history of atopic disease. The infant may be born either vaginally or via C-section.

As used herein, the term "effective amount" refers to an amount of a regimen and/or composition sufficient to significantly induce a positive benefit, including independently or in combination with other benefits disclosed herein. This means that the content and/or concentration of active component in the regimen and/or composition is sufficient that when the regimen and/or composition is applied with normal frequency and in a normal amount, the regimen and/or composition can result in treating or reducing the onset or occurrence of childhood atopic disease. The effective amount of the compound, extract, or composition will vary with, e.g., the age, health and environmental exposure of the end user, the duration and nature of the treatment, the specific extract, ingredient, or composition employed, the particular pharmaceutically-acceptable carrier utilized, and like factors.

As used herein, the term "skin barrier function composition" refers to a composition capable of enhancing or improving a subject's skin barrier when administered to the subject. A skin barrier function composition can comprise one or more ingredients that help the skin to provide protection from external threats such as infectious agents, chemicals, systemic toxicity and allergens, protection from enhanced loss of water from the body, and/or function to maintain homeostasis within the body. As used herein, the term "emollient" refers to chemical agents specially designed to make the external layers of the skin (epidermis) softer and more pliable. Examples of emollient include, but are not limited to, humectant (e.g., glycerin), butters, oils, esters, lipids, and fatty acids.

"Moisturizers" as used herein are those agents that can maintain or increase concentration of free water within epidermis. It may add moisture to the skin, draw water from the dermis into the epidermis, or prevent moisture from leaving. Moisturizers include emollients and occlusives. Examples of occlusives include, e.g., petroleum jelly (vaseline), mineral oil, silicone, dimethicone, waxes, and lanolin.

"Infant" as used herein refers to a human whose age ranges from birth to approximately twelve months of life.

"Topical application", "topically", and "topical", as used herein, mean to apply the regimen and/or composition used in accordance with the present disclosure onto the surface of the skin.

As used herein, a "second composition comprising an effective amount of a probiotic" refers to a composition containing an effective amount of an isolated or enriched probiotic. As used herein, "isolated or enriched probiotic" refers to a probiotic that is isolated or enriched from its naturally environment. In some embodiments, the second composition is breast milk containing a probiotic, such as one or more bacterial cells of *Lactobacillus, Lacticaseibacillus* and *Bifidobacterium* genera, which are isolated or enriched from their natural environment. The second composition is not a naturally occurring breast milk.

Methods of Preventing Childhood Atopic Diseases

The present application describes a method of treating or reducing the onset or occurrence of childhood atopic disease in a subject in need thereof, the method comprising conducting at least two of:
- (a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject; and
- (b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food; and
- (c) orally administering to the subject premeasured doses of one or more food allergens, wherein the administration of the one or more food allergens starts within about 1-8 months, more particularly within about 2-6 months, after the birth of the subject.

In some embodiments, the method comprises conducting (a) and (b).

In some embodiments, the method comprises conducting (a) and (c).

In some embodiments, the method comprises conducting (b) and (c).

In some embodiments, the method comprises conducting (a), (b) and (c).

In certain embodiments, the methods comprises:
- (a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;
- (b) orally administering to the subject one or more food allergens at an exposure dose for one or more days, wherein the administration of the one or more food allergens starts within about 1-8 months, more particularly within about 2-6 months, after the birth of the subject; and
- (c) after step (b), administering to the subject the one or more food allergens at a maintenance dose for one or more days.

In certain embodiments, the methods comprises:
- (a) orally administering to the subject a second composition comprising an effective amount of a probiotic, such as a *Bifidobacterium*, wherein the administration of the second composition starts from within about 30 days, more particularly within about 28 days, 21 days, 14 days, or 7 days, after the birth of the subject and optionally continues to at least prior to introduction of solid food;
- (b) orally administering to the subject one or more food allergens at an exposure dose for one or more days, wherein the administration of the one or more food allergens starts within about 1-8 months, more particularly within about 2-6 months, after the birth of the subject; and
- (c) after step (b), orally administering to the subject the one or more food allergens at a maintenance dose for one or more days.

In certain embodiments, the method comprises:
- (a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject; and
- (b) orally administering to the subject a second composition comprising an effective amount of a probiotic, such as a *Bifidobacterium*, wherein the administration of the second composition starts from within about 30 days, more particularly within about 28 days, 21 days, 14 days, or 7 days, after the birth of the subject and optionally continues to at least prior to introduction of solid food.

In certain embodiments, the methods comprises:
- (a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;
- (b) orally administering to the subject a second composition comprising an effective amount of a probiotic, such as a *Bifidobacterium*, wherein the administration of the second composition starts from within about 30 days, more particularly within about 28 days, 21 days, 14 days, or 7 days, after the birth of the subject and optionally continues to at least prior to introduction of solid food;
- (c) orally administering to the subject one or more food allergens at an exposure dose for one or more days, wherein the administration of the one or more food allergens starts within about 1-8 months, more particularly within about 2-6 months, after the birth of the subject; and
- (d) after step (c), orally administering to the subject the one or more food allergens at a maintenance dose for one or more days.

In certain embodiments, when both of the first composition and the second composition are to be administered, the administration of the first composition starts before the administration of the second composition. In certain embodiments, while the administration of the first composition, second composition and/or allergens start at different time, the administrations of the first composition, second composition and/or allergens can overlap. For example, the first composition can be first administered at about one day to about seven days, preferably at about 4 days, more preferably at about 2 days, after the birth of the subject; and the second composition can be first administered at about one day to about 30 days, preferably at about one day to 14 days, after the birth of subject, and the one or more food allergens can be first administered at about 1 months to about 8 months, preferably at about 2 months to 6 months, after the birth of the subject.

With regard to step (a) of the method, the first composition comprises a skin barrier function composition. The skin barrier is important to human life. Physically, it protects from external threats such as infectious agents, chemicals, systemic toxicity and allergens. Internally, the skin helps to maintain homeostasis and protects from enhanced loss of water from the body. See, e.g., Kanwar et al., Indian J Med Res. 2018 January; 147(1): 117-118, for the basic parameters involved in skin barrier function, the external factors influencing skin barrier and the treatments improving the skin barrier. See, also, e.g., Cezmi A. Akdis, Nature Reviews Immunology, 2021 (21): 739-751, and Cezmi A. Akdis, J. Allergy Clin. Immunol., 2022, Volume 149 (1): 41-44. A skin barrier function composition can contain one or more of a moisturizer, an ingredient that helps to rebuild the barrier and reduce inflammation, such as ceramides or oats, and a skin protectant that prevents (through surface chemistry) proteins or other substances from getting into the skin, such as a silicone-based polymer (e.g., dimethicone), etc.

It is believed that the first composition exerts its effect at least in part by a combination of timing of administration and action of a single ingredient in the composition; and/or by a combination of timing of the administration and action of a combination of two or more ingredients in the composition; and/or by a combination of timing of the administration and action based on the amount of a single ingredient in the composition; and/or by a combination of timing of the administration and action based on the relative amounts of two or more ingredients in the composition.

While not wishing to be bound by theory, the inventors believe that the first composition exerts its effect by one or more of the following:
  a. Improving barrier function;
  b. Having a probiotic effect on skin microbiome, thereby stimulating the growth of microorganisms having beneficial properties;
     i. It is believed that some of the ingredients may achieve this by acting as a buffer to achieve optimal skin pH;
  c. Having an antioxidant effect;
  d. Having an anti-inflammatory effect;
  e. Stimulating ceramide production; and
  f. Stimulating fatty acid production.
  g. Forming a surface layer that prevents food proteins from penetrating the skin barrier In some embodiments, the first composition is administered at least once a day, preferably at least twice a day.

In some embodiments, the administration of the first composition starts within about two days after the birth of the subject.

In some embodiments, the first composition is administered to the skin of the whole body of the subject.

In some embodiments, the first composition is formulated in a dosage form selected from the groups consisting of a balm, a cream, a lotion, an emulsion, a serum, an ointment, and a paste.

According to embodiments of the present application, the first composition comprises one or more ingredients selected from the group consisting of glycerin, aqua, cetearyl alcohol, isocetyl alcohol, dimethicone, cetyl alcohol, *Avena sativa* kernel flour, *Avena sativa* kernel extract, *Avena sativa* kernel oil, caprylic/capric triglyceride, ceramide 3, ethylhexylglycerin, p-anisic acid, sodium cetearyl sulfate, palmitic acid, stearic acid, sodium sulfate, sodium chloride, citric acid, dipotassium phosphate, potassium phosphate, sodium hydroxide, tocopherol, benzyl alcohol, benzoic acid and potassium sorbate and a carrier. In some embodiments, the first composition comprises an emollient, more particularly the first composition further comprises colloidal oatmeal, ceramides, and distearyldimonium chloride.

In some embodiments, the first composition comprises one or more of the following ingredients in the amounts set forth below:
  a. caprylic/capric triglyceride, preferably from about 0.0% to about 1.0%, more preferably from about 0.005% to about 1.0%;
  b. citric acid, preferably from about 0.0% to about 0.1%, more preferably from about 0.005% to about 0.1%;
  c. benzoic acid, preferably from about 0.0% to about 2.0%, more preferably from about 0.1% to about 2.0%;
  d. potassium phosphate, preferably from about 0.0% to about 2.0%, more preferably from about 0.05% to about 2.0%;
  e. dimethicone, preferably from about 0.0% to about 10.0%, more preferably from about 1.0% to about 10.0%;
  f. stearic acid; palmitic acid, preferably from about 0.0% to about 2.0%, more preferably from about 0.1% to about 2.0%;
  g. isocetyl alcohol, preferably from about 0.0% to about 10.0%, more preferably from about 1.0% to about 10.0%;
  h. *Avena sativa* (oat) kernel flour, preferably from about 0.0% to about 2.0%, more preferably from about 0.1% to about 2.0%;
  i. ceramide 3, preferably from about 0.0% to about 0.1%, more preferably from about 0.005% to about 0.1%;
  j. ethylhexylglycerin, preferably from about 0.0% to about 2.0%, more preferably from about 0.1% to about 2.0%;
  k. *Avena sativa* (oat) kernel oil, preferably from about 0.0% to about 1.0%, more preferably from about 0.005% to about 1.0%;
  l. *Avena sativa* (oat) kernel extract, which includes glycerin, potassium sorbate and water, preferably from about 0.0% to about 1.0%, more preferably from about 0.005% to about 1.0%;
  m. water, preferably from about 15.0% to about 40.0%, more preferably from about 20.0% to about 40.0%;
  n. glycerin, preferably from about 20.0% to about 50.0%, more preferably from about 30.0% to about 50.0%;
  o. sodium cetearyl sulfate, preferably from about 0.0% to about 2.0%, more preferably from about 0.1% to about 2.0%;
  p. dipotassium phosphate, preferably from about 0.0% to about 2.0%, more preferably from about 0.1% to about 2.0%;
  q. sodium hydroxide, preferably from about 0.0% to about 1.0%, more preferably from about 0.005% to about 1.0%;
  r. cetyl alcohol, preferably from about 0.0% to about 10.0%, more preferably from about 1.0% to about 10.0%;
  s. cetearyl alcohol, preferably from about 0.0% to about 10.0%, more preferably from about 1.0% to about 10.0%;
  t. benzyl alcohol, preferably from about 0.0% to about 2.0%, more preferably from about 0.1% to about 2.0%; and/or
  u. p-anisic acid, preferably from about 0.0% to about 2.0%, more preferably from about 0.1% to about 2.0%.

While not wishing to be bound by theory, the ingredients alone or combined with other ingredients are believed to exert effects at least in part as follows:

a. Improving barrier function;
   i. caprylic/capric triglyceride creates a barrier on the skin's surface, which helps to reduce skin dryness by decreasing the loss of moisture.
   ii. dimethicone acts as a skin protectant.
   iii. stearic acid and palmitic acid are fatty acids that create an occlusive barrier that protects skin from unwanted microbes and pollutants while retaining moisture.
   iv. hexyldecanol is a fatty alcohol that forms a layer over the skin surface.
   v. ceramide, together with saturated fatty acids, creates a water-impermeable, protective layer to prevent excessive water loss due to evaporation as well as a to provide a barrier against the entry of microorganisms.
   vi. glycerin also known as glycerol is a humectant that can hydrate the outer layer of the skin and improve skin barrier function and skin mechanical properties.
b. Having a probiotic effect on skin microbiome, thereby stimulating the growth of microorganisms having beneficial properties. It is believed that the application of one or more of the ingredients in the composition may play a role in the balance of the skin microbiota.
   i. oatmeal-based products work with skin to do a number of things, including creating a protective barrier, known as the skin microbiome, on the surface of the skin that guards against opportunistic pathogenic microorganisms.
      1. *Avena sativa* (oat) kernel flour
      2. *Avena sativa* (oat) kernel oil
      3. water; glycerin; *Avena sativa* (oat) kernel extract
   ii. buffer skin ph to help skin achieve optimal ph levels that can affect the survival and growth rates of microbial species:
      2. benzoic acid
      3. potassium phosphate
      4. dipotassium phosphate
      5. sodium hydroxide
   iii. glycerin also known as glycerol is a humectant that can have an effect on the microbiome.
c. Having an antioxidant effect;
   i. caprylic/capric triglyceride can act as an antioxidant, which work to neutralize toxins exposed to in an environment.
   ii. tocopherol
d. Having an anti-inflammatory effect;
   i. one or more ingredients in the composition may correct subclinical skin barrier dysfunction and early inflammation in predisposed infants before atopic dermatitis development by improving skin hydration and reducing skin permeability. this skin barrier enhancement prevents skin dryness and cracking, as well as inhibiting irritant and allergen penetration into the epidermis, which are potential initiators of skin inflammation.
   ii. oat ingredients have anti-inflammatory qualities that help to reduce itchiness.
      1. *Avena sativa* (oat) kernel flour
      2. *Avena sativa* (oat) kernel oil
      3. water; glycerin; *Avena sativa* (oat) kernel extract
e. Stimulating ceramide production;
   i. *Avena sativa* (oat) kernel flour
   ii. *Avena sativa* (oat) kernel oil
   iii. water; glycerin; *Avena sativa* (oat) kernel extract
   iv. glycerin also known as glycerol
f. Stimulating fatty acid production.
   i. glycerin also known as glycerol.

Ethylhexylglycerin is a glyceryl ether that is commonly used as part of a preservative system or its skin-conditioning properties in cosmetic preparations.

Sodium cetearyl sulfate is a mixture of stearyl and cetyl sulfate that functions as a surfactant in compositions.

Cetyl alcohol serves as a thickening agent and emulsifier, to help keep product ingredients from separating.

Cetearyl alcohol is a mixture of cetyl alcohol and stearyl alcohol, both fatty alcohols, and are used in personal care products, to create smoother, thicker compositions.

Benzyl alcohol acts as a preservative in skincare products due to its antibacterial and anti-fungal properties.

P-Anisic acid acts as a masking agent (meaning that it helps to mask smells in the product) and as a preservative.

Dimethicone may also have a defoaming effect, which could affect the aesthetics of the product to make it more desirable for use by a consumer.

As used in step (b) of the method, the second composition can contain a probiotic that helps to establish the healthy microbiota. Examples of the probiotic include, but are not limited to, a bacterial strain selected from *Lactobacillus, Lacticaseibacillus* and *Bifidobacterium* genera, more particularly comprises *Bifidobacterium* cell. *Bifidobacterium* is a genus of gram-positive, anaerobic bacteria, which reside in the gastrointestinal, vaginal, and oral tracts of mammals, including humans. The suitable *Bifidobacterium* may be those having at least one human milk oligosaccharides (HMO) gene cluster. The *Bifidobacterium* may be one that is similar to *B. infantis*. The *Bifidobacterium* can be selected from the group consisting of *B. longum, B. breve, B. bifidum, B. pseudocatemilatum, B. globosum, B. adolescentis, B. moukalabense, B. reuteri, B. pseudolongum, B. dentium, B. catenulatum, B.* sp002742445, *B. callitrichos, B. scardovii, B. tissieri, B. subtile, B. gallinarum, B. choerinum, B. angulatum, B. primatium, B. myosotis, B. mongoliense, B. merycicum, B. lemurum, B. stellenboschense, B. scaligerum, B. saguini, B. pullorum, B. felsineum, B. eulemuris, B. cuniculi, B. callitrichos A, B. biavatii, B. anseris, B. vansinderenii, B.* sp900551485, *B.* sp003952945, *B.* sp003952025, B. sp003952005, *B. simiarum, B. pseudolongum C, B. parmae, B. margollesii, B. kashiwanohense A, B. italicum, B. imperatoris, B. cricetid, B. catulorum, B. callitrichidarum, B. animalis, B. aesculapii*, and combinations thereof. The *Bifidobacterium* can be selected from the group consisting of *B. longum, B. breve, B. kashiwanohense* and combinations thereof. The *Bifidobacterium* can be *B. longum*. The *Bifidobacterium* can be a subspecies of *B. longum* selected from the group consisting of *longum, suis* and *infantis*.

In certain embodiments, the *Bifidobacterium* cell in the second composition is *B. infantis* cell. As used herein, the term "*Bifidobacterium infantis*" or "*B. infantis*" is meant to refer to the subspecies of *Bifidobacterium longum* subsp. *infantis*. The *B. infantis* may comprise the strain EVC001. *B. infantis* can be isolated and cultured using methods known in the art.

The *B. infantis* can be co-administered with one or more other probiotics (i.e., other bacteria which are intended to have health benefits). The other probiotics can be strains selected from *Lactobacillus, Lacticaseibacillus* and *Bifidobacterium* genera. Examples of *Bifidobacterium* species include other strains of *B. infantis, B. Longum* (subspecies other than *B. infantis*), *B. Breve, B. catemilatum, B. adolescentis, B. animalis, B. gallicum, B. lactis, B. pseudocatemilatum* and *B. Bifidum*. Examples of *Lactobacillus* strains include *L. paracasei, L. acidophilus, L. johnsonii, L. del-*

*brueckii, L. crispatus, L. gasser, L. zeae*, and combinations thereof. Examples of *Lacticaseibacillus* include *L. casei, L. rhamnosus* and combinations thereof. Other probiotics include *Lactiplantibacillus plantarum, Limosilactobacillus fermentum* and *Ligilactobacillus salivarius*. Alternatively, the *Bifidobacterium* can be administered without any other probiotics. That is, the *Bifidobacterium* can be formulated to be essentially free of any other probiotics.

The subject's gut microbiome profile can be tested and monitored to determine colonization by *Bifidobacterium* using methods known in the art. Stool samples may be used in such methods.

The *Bifidobacterium* can be formulated into a composition which is easy to use and allows for consistent dosing. The fermentation product from *Bifidobacterium* production can be concentrated and freeze dried to provide a concentrated powder.

According to the embodiments of the present application, the second composition comprises about 0.1 to about 100, more particularly about 5 to about 15, billion colony forming units (CFU) of *B. infantis* (CFU) of *Bifidobacterium*, preferably *B. infantis*, per gram dry weight. In certain embodiment, the second composition comprises about 8 billion colony forming units (CFU) of *B. infantis* per gram dry weight.

In one preferred embodiment, the second composition is not naturally occurring breast milk.

The *Bifidobacterium* can also be formulated with an oligosaccharide. As used herein, the term "oligosaccharide" refers to a saccharide polymer containing 2 to 20, 2 to 10, 3 to 20 or 3 to 10 monosaccharide units. The oligosaccharide can be those found in a mammalian milk (e.g., human, or bovine). The oligosaccharide can be synthesized.

The second composition containing the *Bifidobacterium* can also contain an auxiliary component. Such auxiliary components are those commonly used in the art and can be selected from metabolites, flow agents or combinations thereof. Examples of flow agents include starch, silicon dioxide, cellulose, sodium bicarbonate, calcium silicate and the like. The auxiliary component may also be a milk protein or constituent. The auxiliary component may comprise lactose. That is, in such an example, the *Bifidobacterium* is in powder form mixed with lactose.

The final form of the second composition can be any known in the art. As described above, the *Bifidobacterium* can be in dried form (e.g., spray-dried or freeze-dried) as a powder. Said powder may be dosed as a packet, sachet, tablet, foodstuff, capsule, lozenge, tablet, suspension, dry form, etc.

In certain embodiments, the second composition containing *Bifidobacterium* which is suitable in accordance with one or more embodiments of the invention is Evivo® probiotic available from Evolve BioSystems (Davis, CA), which are packaged in a sachet containing 8 billion CFU of *B. infantis* (EVC001) co-formulated with lactose.

According to embodiments of the present application, the subject is breastfed, or fed by a supplementation comprising one or more human breast milk oligosaccharides or prebiotics. It is believed that the human breast milk oligosaccharides or the prebiotics can support the growth of *Bifidobacterium* (see, e.g., Francesca Turroni, et al., Trends in Microbiology, 2018, Volume 26 (4): 339-350, and Andrea C. Masi and Christopher J. Stewart, iScience, 2022, Volume 25b91): 103542). In some embodiments, the prebiotics can be other oligosaccharides, polysaccharides or fibers. In some embodiments, the supplementation can be infant formula.

A given dose of probiotic, such as *Bifidobacterium*, is provided to the subject as part of feeding (i.e., it is used as a food supplement). The probiotic, such as *Bifidobacterium*, can be mixed with any medium that can be consumed by the subject, including breast milk, infant formula, water or food prior to administering the probiotic, such as *Bifidobacterium*, to the subject. The probiotic, such as *Bifidobacterium*, can be mixed into breast milk prior to administering the probiotic, such as *Bifidobacterium*, to the subject. Alternatively, the probiotic, such as *Bifidobacterium*, can be mixed into infant formula prior to administering the *Bifidobacterium* to the subject. The probiotic, such as *Bifidobacterium*, is mixed with enough infant formula or breast milk so that the subject is able to completely incorporate the *Bifidobacterium* and so that the subject is still likely and able to consume the entire dose of *Bifidobacterium*. Thus, the probiotic, such as *Bifidobacterium*, can be mixed with about 3 to about 5 mL of breast milk or infant formula prior to administering the probiotic, such as *Bifidobacterium*, to the subject. The probiotic, such as *Bifidobacterium*, composition can be mixed by any suitable means, including simply stirring (or any other suitable means to obtain a mixture) the composition with the medium (e.g., infant formula, breast milk, water) in a bowl. The composition mixed with infant formula or breast milk can then be fed to the subject by any suitable means. Suitable means of feeding include use of a feeding syringe, spoon, or bottle. The probiotic, such as *Bifidobacterium*, can be administered prior to feeding the subject when the subject is more likely to be hungry, which is thought to increase the likelihood of consuming the entirety of the dose.

The dose and dosing frequency may be selected as desired. In some embodiments, the second composition comprising probiotic, such as *Bifidobacterium*, is administered once daily, and the dose once daily can contain from about 5-15 billion or about 8 billion CFU. Splitting the total desired dose into smaller doses is also contemplated. Examples could include smaller doses several times throughout the day (e.g., 2, 3, 4 or 5 times per day).

The total dose given per day can range from about 1 million, 500 million, 1 billion, 2 billion, 3 billion, 4 billion, 5 billion, 6 billion, 7 billion, 8 billion, 9 billion, 10 billion or 12 billion to about 8 billion, 9 billion, 10 billion, 20 billion, 30 billion, 40 billion, 50 billion, 60 billion, 70 billion, 80 billion, 90 billion, 100 billion, 200 billion, 250 billion or 500 billion colony forming units (CFU) of the probiotic, such as *Bifidobacterium*. The total dose given per day can range from about 5 to about 15 billion CFU, or be about 8 billion CFU. Such total dose values can be given in one dose.

The second composition comprising probiotic, such as *Bifidobacterium*, can be administered beginning from within about 30 days, more particularly within about 28 days, 21 days, 14 days, or 7 days, after the birth of the subject. Once started, the second composition comprising probiotic, such as *Bifidobacterium*, can continue to be administered until the 4th, 5th, 6th, 7th, 8th, 9th, 10th, 11th, 12th week after the birth of the subject, or until the 3rd, 4th, 5th, 6th, 7th, 8th, 9th, 10th, 11th or 12th month after the birth of the subject, or at least prior to the introduction of solid food. The administration of the second composition can continue until a desired gut microbiota is established. The subject can receive one, two, three, four, five, or more administrations of the second composition, to help establish a desired microbiota.

In some embodiments, the second composition is first administered within the first 14 days after the birth of the subject. In some embodiments, the second composition is administered for at least 12 weeks.

The step (c) of the methods described in the present application relates to early introduction of multiple food allergens. Recent randomized controlled trials on early introduction of highly allergenic foods have shown a correlated reduction in food allergy incidence.

According to embodiments of the present application, during the exposure phase, food proteins representing major food allergens are introduced one by one and with graded dose increases. Additional food allergens are added over the course of multiple days. During the maintenance phase, sustained amounts of all of the relevant food allergens are administered. These are continued daily until routine diet diversity is achieved from the regular consumption of solid foods. In some embodiments, the administration of the one or more food allergens comprises:

i. administering to the subject a first food allergen at an exposure dose for the first food allergen for one or more days;

ii. subsequently administering to the subject the first food allergen at a maintenance dose for the first food allergen for multiple days;

iii. subsequently administering to the subject the first food allergen at the maintenance dose and a second food allergen at an exposure dose for the second food allergen for one or more days; and iv. subsequently administering both the first and the second food allergens at maintenance doses for each allergen for multiple days.

In some embodiments, the exposure dose can optionally be gradually increased.

In some embodiments, the exposure dose of the first food allergen and the exposure dose of the second food allergen are lower than the maintenance dose of the first food allergen and the maintenance dose of the second food allergen, respectively.

The "exposure" phase involves optionally graded increases in food allergen amount as well as sequential introduction of new food allergens. Once maintenance levels of each have been attained, continuation at these levels is done through daily administration during the "maintenance" phase.

In some embodiments, the method further comprises continuing the maintenance doses of the first food allergen and the second food allergen until the premeasured doses for each of the food allergens are fully consumed.

In some embodiments, the maintenance doses are continued for several months until the subject is regularly consuming foods containing the first food allergen and the second food allergen as part of the subject's diet.

In some embodiments, the method further comprises:

v. administering to the subject a third food allergen at an exposure dose for the third food allergen for one or more days, and vi. subsequently administering to the subject the first food allergen, the second food allergen, and the third food allergen at maintenance doses for each of the allergens for multiple days.

In certain embodiments, the method further comprises continuing the maintenance doses of the first food allergen, the second food allergen, and the third food allergen until the premeasured doses for each of the food allergens are consumed.

In some embodiments, the premeasured doses for each of the first, second and third food allergens are consumed over 12 days.

In certain embodiments, the administration of the one or more food allergens starts within about 2-6 months, such as 2, 3, 4, 5, or 6 months, after the birth of the subject.

In some embodiments, the first food allergen, second food allergen and third food allergen are each independently selected from the group consisting of cow milk, egg, peanut, wheat, soy, sesame, fish, shellfish, and tree nut, preferably cow milk, egg and peanut, respectively.

The one or more food allergens can be in the form of powder, such as protein powder. The protein powders can be formulated to readily suspend in breast milk or infant formula and can be of a particle size (such as less than about 200 microns) that readily passes through the nipple of common infant bottles. The one or more food allergens can be provided in the form of a kit which includes an outer container (box, bag, pouch, tin) with individually packaged single use portions, which are to be added by the users to infant formula or mother's milk. Alternatively, the one or more food allergens can be provided as already mixed in with infant formula. For example, infant formula could be provided in a staged kit, with the infant formula progressing through different formulations that introduce and then bring up the level of the various allergens until a final, maintenance infant formula is reached, and then that maintenance infant formula can continue to be given to the infant for a time. In addition to a staged kit, an infant formula containing a maintenance level of the multiple food allergens at their maintenance doses can be provided.

In some embodiments, the premeasured doses of the food allergens are mixed into breast milk, supplementation, or food prior to administering the allergens to the subject.

In some embodiments, the premeasured doses of the food allergens are in the form of powder.

In some embodiments, the exposure dose of each food allergen is between about 0.01 and 0.3 grams and the maintenance dose of each food allergen is between about 0.05 and 1 grams.

In some embodiments, the first food allergen comprises cow milk and the exposure dose of the first food allergen is about 0.2 grams of cow milk proteins, wherein the maintenance dose of the first food allergen is about 0.4 grams of cow milk proteins.

In some embodiments, the second food allergen comprises egg and the exposure dose of the second food allergen is about 0.03 grams of the egg proteins, wherein the maintenance dose of second food allergen is about 0.1 grams of the egg proteins.

In some embodiments, the third food allergen comprises peanut and the exposure dose of the third food allergen is about 0.1 grams of the peanut proteins, and wherein the maintenance dose of third food allergen is about 0.4 grams of the peanut proteins.

The timing of the administration in each of the step (a), (b) and (c) can be overlapped. For example, the administration of the first composition and the administration of the second composition comprising a probiotic, such as a *Bifidobacterium*, can be conducted in one time period;

the administration of the first composition and the administration of the one or more food allergens can be conducted in one time period; and/or the administration of the second composition comprising a probiotic, such as a *Bifidobacterium* and the administration of the one or more food allergens can be conducted in one time period.

In another general aspect, the application describes a kit or a combination comprising at least two of:
- (a) a first composition which comprises a skin barrier function composition;
- (b) a second composition comprising an effective amount of a probiotic, such as a *Bifidobacterium* cell; and
- (c) premeasured doses of one or more food allergens.

In some embodiments, the kit or the combination is for use in treating or reducing the onset or occurrence of childhood atopic disease in a subject in need thereof.

The first composition, second composition, and the food allergens in the kit or combinations can be those described in the application, such as the above embodiments.

While the foregoing description represent exemplary embodiments of the present invention, it will be understood that various additions, modifications, and substitutions may be made herein without departing from the spirit and scope of the present invention. In particular, it will be clear to those skilled in the art that the present invention can be embodied in other specific forms, structures, arrangements, proportions, and with other elements, materials, and components, without departing from the spirit or essential characteristics thereof. One skilled in the art will appreciate that the invention can be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description. It will be appreciated that in the claims, the term "comprises/comprising" does not exclude the presence of other elements or steps. In addition, singular references do not exclude a plurality. The terms "a", "an", "first", "second", etc., do not preclude a plurality.

EMBODIMENTS

The application provides also the following non-limiting embodiments.

Embodiment 1 is a method of treating or reducing the onset or occurrence of childhood atopic disease in a subject in need thereof, the method comprising conducting at least two of:
- (a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject; and
- (b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food; and
- (c) orally administering to the subject premeasured doses of one or more food allergens, wherein the administration of the one or more food allergens starts within about 1-8 months, more particularly within about 2-6 months, after the birth of the subject.

Embodiment 1a is the method of embodiment 1, wherein the method comprises conducting (a) and (b).

Embodiment 1a (1) is the method of embodiment 1a, wherein the administration of the first composition starts before the administration of the second composition.

Embodiment 1a (2) is the method of embodiment 1a, wherein the administration of the first composition starts after the administration of the second composition.

Embodiment 1b is the method of embodiment 1, wherein the method comprises conducting (a) and (c).

Embodiment 1c is the method of embodiment 1, wherein the method comprises conducting (b) and (c).

Embodiment 1d is the method of embodiment 1, wherein the method comprises conducting (a), (b) and (c).

Embodiment 1d (1) is the method of embodiment 1d, wherein the administration of the first composition starts before the administration of the second composition.

Embodiment 1d (2) is the method of embodiment 1d, wherein the administration of the first composition starts after the administration of the second composition.

Embodiment 1e is the method of embodiment 1, wherein the methods comprises:
- (a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;
- (b) orally administering to the subject one or more food allergens at an exposure dose for one or more days, wherein the administration of the one or more food allergens starts within about 1-8 months, more particularly within about 2-6 months, after the birth of the subject; and
- (c) orally after step (b), administering to the subject the one or more food allergens at a maintenance dose for one or more days.

Embodiment 1f is the method of embodiment 1, wherein the methods comprises:
- (a) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food;
- (b) orally administering to the subject one or more food allergens at an exposure dose for one or more days, wherein the administration of the one or more food allergens starts within about 1-8 months, more particularly within about 2-6 months, after the birth of the subject; and
- (c) after step (b), orally administering to the subject the one or more food allergens at a maintenance dose for one or more days.

Embodiment 1g is the method of embodiment 1, wherein the method comprises:
- (a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject; and (b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food.

Embodiment 1h is the method of embodiment 1, wherein the methods comprises:

(a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;

(b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food;

(c) orally administering to the subject one or more food allergens at an exposure dose for one or more days, wherein the administration of the one or more food allergens starts within about 1-8 months, more particularly within about 2-6 months, after the birth of the subject; and (d) after step (c), orally administering to the subject the one or more food allergens at a maintenance dose for one or more days.

Embodiment 2 is the method of any one of embodiments 1-1b, 1d-1e, and 1g-1h, wherein the first composition is administered at least once a day Embodiment 2a is the method of any one of embodiments 1-1b, 1d-1e, and 1g-2, wherein the first composition is administered at least twice a day.

Embodiment 2b is the method of any one of embodiments 1-1b, 1d-1e, and 1g-2a, wherein the first composition starts within about two days after the birth of the subject.

Embodiment 3 is the method of any one of embodiments 1-1b, 1d-1e, and 1g-2b, wherein the first composition is administered to the skin of the whole body of the subject.

Embodiment 3a is the method of any one of embodiments 1-1b, 1b-1e, and 1g-3, wherein the first composition is formulated in a dosage form selected from the groups consisting of a balm, a cream, a lotion, an emulsion, a serum, an ointment, and a paste.

Embodiment 4 is the method of any one of embodiments 1-1b, 1d-1e, and 1g-3a, wherein the first composition comprises one or more ingredients selected from the group consisting of glycerin, aqua, cetearyl alcohol, isocetyl alcohol, dimethicone, cetyl alcohol, *Avena sativa* kernel flour, *Avena sativa* kernel extract, *Avena sativa* kernel oil, caprylic/capric triglyceride, ceramide 3, ethylhexylglycerin, p-anisic acid, sodium cetearyl sulfate, palmitic acid, stearic acid, sodium sulfate, sodium chloride, citric acid, dipotassium phosphate, potassium phosphate, sodium hydroxide, tocopherol, benzyl alcohol, benzoic acid and potassium sorbate and a carrier.

Embodiment 4a is the method of any one of embodiments 1-1b, 1d-1e, and 1d-3a, wherein first composition comprises two or more ingredients selected from the group consisting of glycerin, aqua, cetearyl alcohol, isocetyl alcohol, dimethicone, cetyl alcohol, *Avena sativa* kernel flour, *Avena sativa* kernel extract, *Avena sativa* kernel oil, caprylic/capric triglyceride, ceramide 3, ethylhexylglycerin, p-anisic acid, sodium cetearyl sulfate, palmitic acid, stearic acid, sodium sulfate, sodium chloride, citric acid, dipotassium phosphate, potassium phosphate, sodium hydroxide, tocopherol, benzyl alcohol, benzoic acid and potassium sorbate and a carrier.

Embodiment 4b is the method of any one of embodiments 1-1b, 1d-1e, and 1d-3a, wherein first composition comprises three or more ingredients selected from the group consisting of glycerin, aqua, cetearyl alcohol, isocetyl alcohol, dimethicone, cetyl alcohol, *Avena sativa* kernel flour, *Avena sativa* kernel extract, *Avena sativa* kernel oil, caprylic/capric triglyceride, ceramide 3, ethylhexylglycerin, p-anisic acid, sodium cetearyl sulfate, palmitic acid, stearic acid, sodium sulfate, sodium chloride, citric acid, dipotassium phosphate, potassium phosphate, sodium hydroxide, tocopherol, benzyl alcohol, benzoic acid and potassium sorbate and a carrier.

Embodiment 4c is the method of any one of embodiments 1-1b, 1d-1e, and 1d-3a, wherein the first composition comprises an emollient, more particularly, the first composition further comprises colloidal oatmeal, ceramides, and distearyldimonium chloride.

Embodiment 4d is the method of any one of embodiments 1-1b, 1d-1e, and 1d-3a, wherein the first composition comprises one or more of the following ingredients in the amounts set forth below:

a. caprylic/capric triglyceride, preferably from about 0.0% to about 1.0%, more preferably from about 0.005% to about 1.0%;

b. citric acid, preferably from about 0.0% to about 0.1%, more preferably from about 0.005% to about 0.1%;

c. benzoic acid, preferably from about 0.0% to about 2.0%, more preferably from about 0.1% to about 2.0%;

d. potassium phosphate, preferably from about 0.0% to about 2.0%, more preferably from about 0.05% to about 2.0%;

e. dimethicone, preferably from about 0.0% to about 10.0%, more preferably from about 1.0% to about 10.0%;

f. stearic acid; palmitic acid, preferably from about 0.0% to about 2.0%, more preferably from about 0.1% to about 2.0%;

g. isocetyl alcohol, preferably from about 0.0% to about 10.0%, more preferably from about 1.0% to about 10.0%;

h. *Avena sativa* (oat) kernel flour, preferably from about 0.0% to about 2.0%, more preferably from about 0.1% to about 2.0%;

i. ceramide 3, preferably from about 0.0% to about 0.1%, more preferably from about 0.005% to about 0.1%;

j. ethylhexylglycerin, preferably from about 0.0% to about 2.0%, more preferably from about 0.1% to about 2.0%;

k. *Avena sativa* (oat) kernel oil, preferably from about 0.0% to about 1.0%, more preferably from about 0.005% to about 1.0%;

l. *Avena sativa* (oat) kernel Extract, which includes glycerin, potassium sorbate and water, preferably from about 0.0% to about 1.0%, more preferably from about 0.005% to about 1.0%;

m. water, preferably from about 15.0% to about 40.0%, more preferably from about 20.0% to about 40.0%;

n. glycerin, preferably from about 20.0% to about 50.0%, more preferably from about 30.0% to about 50.0%;
o. sodium cetearyl sulfate, preferably from about 0.0% to about 2.0%, more preferably from about 0.1% to about 2.0%;
p. dipotassium phosphate, preferably from about 0.0% to about 2.0%, more preferably from about 0.1% to about 2.0%;
q. sodium hydroxide, preferably from about 0.0% to about 1.0%, more preferably from about 0.005% to about 1.0%;
r. cetyl alcohol, preferably from about 0.0% to about 10.0%, more preferably from about 1.0% to about 10.0%;
s. cetearyl alcohol, preferably from about 0.0% to about 10.0%, more preferably from about 1.0% to about 10.0%;
t. benzyl alcohol, preferably from about 0.0% to about 2.0%, more preferably from about 0.1% to about 2.0%; and/or
u. p-anisic acid, preferably from about 0.0% to about 2.0%, more preferably from about 0.1% to about 2.0%.

Embodiment 5 is the method of any one of embodiments 1-1a, 1c-1d, and 1f-4d, wherein the probiotic includes, but is not limited to, a bacterial strain selected from *Lactobacillus*, *Lacticaseibacillus* and *Bifidobacterium* genera.

Embodiment 5-1 is the method of embodiment 5, wherein the *Bifidobacterium* in the second composition is selected from the group consisting of *B. longum, B. breve, B. bifidum, B. pseudocatemilatum, B. globosum, B. adolescentis, B. moukalabense, B. reuteri, B. pseudolongum, B. dentium, B. catemulatum, B.* sp002742445, *B. callitrichos, B. scardovii, B. tissieri, B. subtile, B. gallinarum, B. choerimim, B. angulatum, B. primatium, B. myosotis, B. mongoliense, B. merycicum, B. lemurum, B. stellenboschense, B. scaligerum, B. saguini, B. pullorum, B. felsineum, B. eulemuris, B. cuniculi, B. callitrichos A, B. biavatii, B. anseris, B. vansinderenii, B.* sp900551485, *B.* sp003952945, *B.* sp003952025, *B.* sp003952005, *B. simiarum, B. pseudolongum C, B. parmae, B. margollesii, B. kashiwanohense A, B. italicum, B. imperatoris, B. cricetid, B. catulorum, B. callitrichidarum, B. animalis, B. aesculapii*, and combinations thereof.

Embodiment 5a is the method of embodiment 5 or 5-1, wherein the *Bifidobacterium* is selected from the group consisting of *B. longum, B. breve, B. kashiwanohense* and combinations thereof.

Embodiment 5b is the method of any one of embodiments 5-5a, wherein the *Bifidobacterium* is *B. longum*, preferably a subspecies of *B. longum* selected from the group consisting of *longum, suis* and *infantis*.

Embodiment 5c is the method of any one of embodiments 5-5b, wherein the *Bifidobacterium* cell is *B. infantis* cell.

Embodiment 5d is the method of embodiment 5c, wherein the *B. infantis* comprise the strain EVC001.

Embodiment 6 is the method of any one of embodiments 1-1a, 1c-1d, and 1f-5d, wherein the second composition comprises about 0.1 to about 100, more particularly about 5 to about 15, billion colony forming units (CFU) of *B. infantis*.

Embodiment 6a is the method of any one of embodiments 1-1a, 1c-1d, and 1f-6, wherein the second composition comprises about 8 billion colony forming units (CFU) of *B. infantis*.

Embodiment 7 is the method of any one of embodiments 1-1a and 1c-6a, wherein the second composition is administered at least once a day.

Embodiment 7a is the method of any one of embodiments 1-1a, 1c-1d, and 1f-7, wherein the administration of the second composition starts within 14 days after the birth of the subject.

Embodiment 7b is the method of any one of embodiments 1-1a, 1c-1d, and 1f-7a, wherein the administration of the second composition continues at least for 12 weeks.

Embodiment 7c is the method of any one of embodiments 1-1a, 1c-1d, and 1f-7b, wherein the administration of the second composition continues until a desired gut microbiota is established.

Embodiment 7d is the method of any one of embodiments 1-1a, 1c-1d, and 1f-7c, wherein the subject receives one, two, three, four, five or more administrations of the second composition.

Embodiment 8 is the method of any one of embodiments 1-7d, wherein the subject is breastfed or fed by a supplementation comprising one or more human breast milk oligosaccharides or prebiotics.

Embodiment 8a is the method of any one of embodiments 1-8, wherein the subject is exclusively breastfed.

Embodiment 8b is the method of any one of embodiments 1-8a, wherein the supplementation comprises infant formula.

Embodiment 8c is the method of embodiment 8, wherein the prebiotics is other oligosaccharide, polysaccharide, or fiber.

Embodiment 8d is the method of embodiment 8, wherein the supplementation is infant formula.

Embodiment 9 is the method of any one of embodiments 1-1a, 1c-1d, and 1f-8d, wherein the *Bifidobacterium* is mixed into the breast milk prior to administering the second composition to the subject.

Embodiment 9a is the method of any one of embodiments 1-1a, 1c-1d, and 1f-8d, wherein the *Bifidobacterium* is mixed into the supplementation such as infant formula prior to administering the second composition to the subject.

Embodiment 9b is the method of any one of embodiments 1-1a, 1c-1d, and 1f-8d, wherein the *Bifidobacterium* is mixed with about 3 to about 5 mL of breast milk, infant formula or water prior to administering the second composition to the subject.

Embodiment 10 is the method of any one of embodiments 1-1a, 1c-1d, and 1f-9b, wherein the *Bifidobacterium* is in a powder form.

Embodiment 10a is the method of embodiment 10, wherein the *Bifidobacterium* is in a powder form mixed with lactose.

Embodiment 10b is the method of any one of embodiments 1-1a, 1c-1d, and 1f-10a, wherein the second composition is not naturally occurring breast milk.

Embodiment 11 is the method of any one of embodiments 1, 1b-1f, and 1h-10a, wherein the administration of the one or more food allergens comprises:
  i. administering to the subject a first food allergen at an exposure dose for the first food allergen for one or more days;
  ii. subsequently administering to the subject the first food allergen at a maintenance dose for the first food allergen for multiple days;
  iii. subsequently administering to the subject the first food allergen at the maintenance dose and a second food allergen at an exposure dose for the second food allergen for one or more days; and
  iv. subsequently administering both the first and the second food allergens at maintenance doses for each food allergen for multiple days.

Embodiment 11a is the method of embodiment 11, wherein the exposure dose is optionally gradually increased.

Embodiment 11b is the method of embodiment 11 or 11a, wherein the exposure dose of the first food allergen and the exposure dose of the second food allergen are lower than the maintenance dose of the first food allergen and the maintenance dose of the second food allergen, respectively.

Embodiment 11c is the method of any one of embodiments 11-11b, wherein the method further comprises continuing the maintenance doses of the first food allergen and the second food allergen until the premeasured doses for each of the food allergens are fully consumed.

Embodiment 11d is the method of any one of embodiments 11-11c, wherein the maintenance doses are continued for several months until the subject is regularly consuming foods containing the first food allergen and the second food allergen as part of the subject's diet.

Embodiment 12 is the method of any one of embodiments 11-11d, wherein the method further comprises:
v. administering to the subject a third food allergen at an exposure dose for the third food allergen for one or more days, and
vi. subsequently administering to the subject the first food allergen, the second food allergen, and the third food allergen at maintenance doses for each of the food allergens for multiple days.

Embodiment 12a is the method of embodiment 12, wherein the method further comprises continuing the maintenance doses of the first food allergen, the second food allergen, and the third food allergen until the premeasured doses for each of the food allergens are consumed.

Embodiment 12b is the method of embodiment 12 or 12a, wherein the premeasured doses for each of the first, second and third food allergens are consumed over 12 days.

Embodiment 13 is the method of any one of embodiments 1, 1b-1f, and 1h-12b, wherein the administration of the one or more food allergens starts within about 2-6 months after the birth of the subject.

Embodiment 14 is the method of any one of embodiments 1, 1b-1f, and 1h-12b, wherein the first food allergen and the second food allergen are each independently selected from the group consisting of cow milk, egg, peanut, wheat, soy, sesame, fish, shellfish, and tree nut.

Embodiment 14a is the method of embodiment 14, wherein the first food allergen is cow milk.

Embodiment 14b is the method of embodiment 14 or 14a, wherein the second food allergen is egg.

Embodiment 15 is the method of any one of embodiments 1, 1b-1f, and 1h-14b, wherein the third food allergen is selected from the group consisting of cow milk, egg, peanut, wheat, soy, sesame, fish, shellfish, and tree nut.

Embodiment 15a is the method of embodiment 15, wherein the third food allergen is peanut.

Embodiment 16 is the method of any one of embodiments 1, 1b-1f, and 1h-15a, wherein the premeasured doses of the food allergens are mixed into breast milk, supplementation, or food prior to administering the allergens to the subject.

Embodiment 17 is the method of any one of embodiments 1, 1b-1f, and 1h-16, wherein the premeasured doses of the food allergens are in the form of powder.

Embodiment 17a is the method of embodiment 17, wherein the allergens consist of particles having a particle size of less than about 200 microns.

Embodiment 18 is the method of any one of embodiments 1, 1b-1f, and 1h-17a, wherein the exposure dose of each allergen is between about 0.01 and 0.3 grams and the maintenance dose of each food allergen is between about 0.05 and 1 grams.

Embodiment 18a is the method of any one of embodiments 1, 1b-1f, and 1h-18, wherein the first food allergen comprises cow milk and the exposure dose of the first food allergen is about 0.2 grams of cow milk proteins, wherein the maintenance dose of the first food allergen is about 0.4 grams of cow milk proteins.

Embodiment 18b is the method of any one of embodiments 1, 1b-1f, and 1h-18a, wherein the second food allergen comprises egg and the exposure dose of the second food allergen is about 0.03 grams of the egg proteins, wherein the maintenance dose of second food allergen is about 0.1 grams of the egg proteins.

Embodiment 18c is the method of any one of embodiments 1, 1b-1f, and 1h-18b, wherein the third food allergen comprises peanut and the exposure dose of the third food allergen is about 0.1 grams of the peanut proteins, and wherein the maintenance dose of third food allergen is about 0.4 grams of the peanut proteins.

Embodiment 19 is a first composition for use in a method of treating or reducing the onset or occurrence of childhood atopic disease, such as atopic dermatitis, in a subject in need thereof, the method comprising conducting at least two of:
(a) topically administering to a skin area of the subject the first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;
(b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food; and
(c) orally administering to the subject premeasured doses of one or more food allergens, wherein the administration of the one or more food allergens starts within about 1-8 months, more particularly within about 2-6 months, after the birth of the subject.

Embodiment 19a is the first composition for use of embodiment 19, wherein the first composition is administered at least once a day Embodiment 19b is the first composition for use of embodiment 19 or 19a, wherein the first composition is administered at least twice a day.

Embodiment 19c is the first composition for use of any one of embodiments 19-19b, wherein the first composition starts within about two days after the birth of the subject.

Embodiment 19d is the first composition for use of any one of embodiments 19-19c, wherein the first composition is administered to the skin of the whole body of the subject.

Embodiment 19e is the first composition for use of any one of embodiments 19-19d, wherein the first composition is formulated in a dosage form selected from the groups consisting of a balm, a cream, a lotion, an emulsion, a serum, an ointment, and a paste.

Embodiment 19f is the first composition for use of any one of embodiments 19-19e, wherein the first composition comprises one or more ingredients selected from the group consisting of glycerin, aqua, cetearyl alcohol, isocetyl alcohol, dimethicone, cetyl alcohol, *Avena sativa* kernel flour, *Avena sativa* kernel extract, *Avena sativa* kernel oil, caprylic/capric triglyceride, ceramide 3, ethylhexylglycerin, p-anisic acid, sodium cetearyl sulfate, palmitic acid, stearic acid, sodium sulfate, sodium chloride, citric acid, dipotassium phosphate, potassium phosphate, sodium hydroxide, tocopherol, benzyl alcohol, benzoic acid and potassium sorbate and a carrier.

Embodiment 19g is the first composition for use of any one of embodiments 19-19f, wherein first composition comprises two or more ingredients selected from the group consisting of glycerin, aqua, cetearyl alcohol, isocetyl alcohol, dimethicone, cetyl alcohol, *Avena sativa* kernel flour, *Avena sativa* kernel extract, *Avena sativa* kernel oil, caprylic/capric triglyceride, ceramide 3, ethylhexylglycerin, p-anisic acid, sodium cetearyl sulfate, palmitic acid, stearic acid, sodium sulfate, sodium chloride, citric acid, dipotassium phosphate, potassium phosphate, sodium hydroxide, tocopherol, benzyl alcohol, benzoic acid and potassium sorbate and a carrier.

Embodiment 19h is the first composition for use of any one of embodiments 19-19b, wherein first composition comprises three or more ingredients selected from the group consisting of glycerin, aqua, cetearyl alcohol, isocetyl alcohol, dimethicone, cetyl alcohol, *Avena sativa* kernel flour, *Avena sativa* kernel extract, *Avena sativa* kernel oil, caprylic/capric triglyceride, ceramide 3, ethylhexylglycerin, p-anisic acid, sodium cetearyl sulfate, palmitic acid, stearic acid, sodium sulfate, sodium chloride, citric acid, dipotassium phosphate, potassium phosphate, sodium hydroxide, tocopherol, benzyl alcohol, benzoic acid and potassium sorbate and a carrier.

Embodiment 19i is the first composition for use of any one of embodiments 19-19b, wherein the first composition comprises an emollient, more particularly, the second composition further comprises colloidal oatmeal, ceramides, and distearyldimonium chloride.

Embodiment 19j is the first composition for use of any one of embodiments 19-19b, wherein the first composition comprises one or more of the following ingredients in the amounts set forth below:
a. caprylic/capric triglyceride, preferably from about 0.0% to about 1.0%, more preferably from about 0.005% to about 1.0%;
b. citric acid, preferably from about 0.0% to about 0.1%, more preferably from about 0.005% to about 0.1%;
c. benzoic acid, preferably from about 0.0% to about 2.0%, more preferably from about 0.1% to about 2.0%;
d. potassium phosphate, preferably from about 0.0% to about 2.0%, more preferably from about 0.05% to about 2.0%;
e. dimethicone, preferably from about 0.0% to about 10.0%, more preferably from about 1.0% to about 10.0%;
f. stearic acid; palmitic acid, preferably from about 0.0% to about 2.0%, more preferably from about 0.1% to about 2.0%;
g. isocetyl alcohol, preferably from about 0.0% to about 10.0%, more preferably from about 1.0% to about 10.0%;
h. *Avena sativa* (oat) kernel flour, preferably from about 0.0% to about 2.0%, more preferably from about 0.1% to about 2.0%;
i. ceramide 3, preferably from about 0.0% to about 0.1%, more preferably from about 0.005% to about 0.1%;
j. ethylhexylglycerin, preferably from about 0.0% to about 2.0%, more preferably from about 0.1% to about 2.0%;
k. *Avena sativa* (oat) kernel oil, preferably from about 0.0% to about 1.0%, more preferably from about 0.005% to about 1.0%;
l. *Avena sativa* (oat) kernel Extract, which includes glycerin, potassium sorbate and water, preferably from about 0.0% to about 1.0%, more preferably from about 0.005% to about 1.0%;
m. water, preferably from about 15.0% to about 40.0%, more preferably from about 20.0% to about 40.0%;
n. glycerin, preferably from about 20.0% to about 50.0%, more preferably from about 30.0% to about 50.0%;
o. sodium cetearyl sulfate, preferably from about 0.0% to about 2.0%, more preferably from about 0.1% to about 2.0%;
p. dipotassium phosphate, preferably from about 0.0% to about 2.0%, more preferably from about 0.1% to about 2.0%;
q. sodium hydroxide, preferably from about 0.0% to about 1.0%, more preferably from about 0.005% to about 1.0%;
r. cetyl alcohol, preferably from about 0.0% to about 10.0%, more preferably from about 1.0% to about 10.0%;
s. cetearyl alcohol, preferably from about 0.0% to about 10.0%, more preferably from about 1.0% to about 10.0%;
t. benzyl alcohol, preferably from about 0.0% to about 2.0%, more preferably from about 0.1% to about 2.0%; and/or
u. p-anisic acid, preferably from about 0.0% to about 2.0%, more preferably from about 0.1% to about 2.0%.

Embodiment 20 is a second composition comprising an effective amount of a probiotic, such as a *Bifidobacterium* cell for use in a method of treating or reducing the onset or occurrence of childhood atopic disease, such as atopic dermatitis, in a subject in need thereof, the method comprising conducting at least two of:
(a) topically administering to a skin area of the subject a first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;
(b) orally administering to the subject the second composition, wherein the administration of the second composition starts from within about 30 days, more particularly within about 28 days, 21 days, 14 days, or 7 days, after the birth of the subject and optionally continues to at least prior to introduction of solid food; and
(c) orally administering to the subject premeasured doses of one or more food allergens, wherein the administration of the one or more food allergens starts within about 1-8 months, more particularly within about 2-6 months, after the birth of the subject.

Embodiment 20a is the second composition for use of embodiment 20, wherein the probiotic includes, but is not limited to, a bacterial strain selected from *Lactobacillus, Lacticaseibacillus* and *Bifidobacterium* genera.

Embodiment 20a-1 is the method of embodiment 20 or 20a, wherein the *Bifidobacterium* in the second composition is selected from the group consisting of *B. longum, B. breve,*

*B. bifidum, B. pseudocatemilatum, B. globosum, B. adolescentis, B. moukalabense, B. reuteri, B. pseudolongum, B. dentium, B. catemilatum, B.* sp002742445, *B. callitrichos, B. scardovii, B. tissieri, B. subtile, B. gallinarum, B. choerinum, B. angulatum, B. primatium, B. myosotis, B. mongoliense, B. merycicum, B. lemurum, B. stellenboschense, B. scaligerum, B. saguini, B. pullorum, B. felsineum, B. eulemuris, B. cuniculi, B. callitrichos A, B. biavatii, B. anseris, B. vansinderenii, B.* sp900551485, *B.* sp003952945, *B.* sp003952025, *B.* sp003952005, *B. simiarum, B. pseudolongum C, B. parmae, B. margollesii, B. kashiwanohense A, B. italicum, B. imperatoris, B. cricetid, B. catulorum, B. callitrichidarum, B. animalis, B. aesculapii,* and combinations thereof.

Embodiment 20b is the second composition for use of any one of embodiments 20-20a-1, wherein the *Bifidobacterium* is selected from the group consisting of *B. longum, B. breve, B. kashiwanohense* and combinations thereof.

Embodiment 20c is the second composition for use of any one of embodiments 20-20b, wherein the *Bifidobacterium* is *B. longum*, preferably a subspecies of *B. longum* selected from the group consisting of *longum, suis* and *infantis*.

Embodiment 20d is the second composition for use of any one of embodiments 20-20c, wherein the *Bifidobacterium* cell is *B. infantis* cell.

Embodiment 20e is the second composition for use of any one of embodiments 20-20d, wherein the *B. infantis* comprise the strain EVC001.

Embodiment 20f is the second composition for use of any one of embodiments 20-20e, wherein the second composition comprises about 0.1 to about 100, more particularly about 5 to about 15, billion colony forming units (CFU) of *B. infantis*.

Embodiment 20g is the second composition for use of any one of embodiments 20-20f, wherein the second composition comprises about 8 billion colony forming units (CFU) of *B. infantis*.

Embodiment 20h is the second composition for use of any one of embodiments 20-20g, wherein the second composition is administered at least once a day.

Embodiment 20i is the second composition for use of any one of embodiments 20-20h, wherein the administration of the second composition starts within 14 days after the birth of the subject.

Embodiment 20j is the second composition for use of any one of embodiments 20-20i, wherein the administration of the second composition continues at least for 12 weeks.

Embodiment 20k is the second composition for use of any one of embodiments 20-20j, wherein the subject is breastfed or fed by a supplementation comprising one or more human breast milk oligosaccharides or prebiotics.

Embodiment 20k(1) is the second composition for use of embodiment 20k, wherein the prebiotics is other oligosaccharide, polysaccharide, or fiber.

Embodiment 20l is the second composition for use of any one of embodiments 20-20k, wherein the subject is exclusively breastfed.

Embodiment 20m is the second composition for use of any one of embodiments 20-20l, wherein the supplementation comprises infant formula.

Embodiment 20n is the second composition for use of any one of embodiments 20-20m, wherein the *Bifidobacterium* is mixed into the breast milk prior to administering the second composition to the subject.

Embodiment 20o is the second composition for use of any one of embodiments 20-20n, wherein the *Bifidobacterium* is mixed into the supplementation such as infant formula prior to administering the second composition to the subject.

Embodiment 20p is the second composition for use of any one of embodiments 20-20o, wherein the *Bifidobacterium* is mixed with about 3 to about 5 mL of breast milk, infant formula or water prior to administering the second composition to the subject.

Embodiment 20q is the second composition for use of any one of embodiments 20-20p, wherein the *Bifidobacterium* is in a powder form.

Embodiment 20r is the second composition for use of any one of embodiments 20-20q, wherein the *Bifidobacterium* is in a powder form mixed with lactose.

Embodiment 20s is the second composition for use of any one of embodiments 20-20r, wherein the second composition is not naturally occurring breast milk.

Embodiment 21 is one or more food allergens at premeasured doses for use in a method of treating or reducing the onset or occurrence of childhood atopic disease, such as atopic dermatitis, in a subject in need thereof, the method comprising conducting at least two of:
  (a) topically administering to a skin area of the subject the first composition, wherein the first composition comprises a skin barrier function composition, and the administration of the first composition starts from within about seven days, more particularly within about six days, five days, four days, three days, two days or one day, after birth of the subject and continues to at least about two months after birth of the subject;
  (b) orally administering to the subject a second composition comprising an effective amount of a probiotic, such as a *Bifidobacterium* cell, wherein the administration of the second composition starts from within about 30 days, more particularly within about 28 days, 21 days, 14 days, or 7 days, after the birth of the subject and optionally continues to at least prior to introduction of solid food; and
  (c) orally administering to the subject the premeasured doses of one or more food allergens, wherein the administration of the one or more food allergens starts within about 1-8 months, more particularly within about 2-6 months, after the birth of the subject.

Embodiment 21a is the one or more food allergens at premeasured doses for use of embodiment 21, wherein the administration of the one or more food allergens comprises:
  i. administering to the subject a first food allergen at an exposure dose for the first food allergen for one or more days;
  ii. subsequently administering to the subject the first food allergen at a maintenance dose for the first food allergen for multiple days;
  iii. subsequently administering to the subject the first food allergen at the maintenance dose and a second food allergen at an exposure dose for the second food allergen for one or more days; and
  iv. subsequently administering both the first and the second food allergens at maintenance doses for each food allergen for multiple days.

Embodiment 21b is the one or more food allergens at premeasured doses for use of embodiment 21a, wherein the exposure dose is optionally gradually increased.

Embodiment 21c is the one or more food allergens at premeasured doses for use of embodiment 21a or 21b, wherein the exposure dose of the first food allergen and the exposure dose of the second food allergen are lower than the maintenance dose of the first food allergen and the maintenance dose of the second food allergen, respectively.

Embodiment 21d is the one or more food allergens at premeasured doses for use of any one of embodiments 21-21c, wherein the method further comprises continuing the maintenance doses of the first food allergen and the second food allergen until the premeasured doses for each of the food allergens are fully consumed.

Embodiment 21e is the one or more food allergens at premeasured doses for use of any one of embodiments 21-21d, wherein the maintenance doses are continued for several months until the subject is regularly consuming foods containing the first food allergen and the second food allergen as part of the subject's diet.

Embodiment 21f is the one or more food allergens at premeasured doses for use of any one of embodiments 21-21e, wherein the method further comprises:
v. administering to the subject a third food allergen at an exposure dose for the third food allergen for one or more days, and
vi. subsequently administering to the subject the first food allergen, the second food allergen, and the third food allergen at maintenance doses for each of the food allergens for multiple days.

Embodiment 21g is the one or more food allergens at premeasured doses for use of any one of embodiments 21-21f, wherein the method further comprises continuing the maintenance doses of the first food allergen, the second food allergen, and the third food allergen until the premeasured doses for each of the food allergens are consumed.

Embodiment 21h is the one or more food allergens at premeasured doses for use of any one of embodiments 21-21g, wherein the premeasured doses for each of the first, second and third food allergens are consumed over 12 days.

Embodiment 21i is the one or more food allergens at premeasured doses for use of any one of embodiments 21-21h, wherein the administration of the one or more food allergens starts within about 2-6 months after the birth of the subject.

Embodiment 21j is the one or more food allergens at premeasured doses for use of any one of embodiments 21-21i, wherein the first food allergen and the second food allergen are each independently selected from the group consisting of cow milk, egg, peanut, wheat, soy, sesame, fish, shellfish, and tree nut.

Embodiment 21k is the one or more food allergens at premeasured doses for use of any one of embodiments 21-21j, wherein the first food allergen is cow milk.

Embodiment 21l is the one or more food allergens at premeasured doses for use of any one of embodiments 21-21k, wherein the second food allergen is egg.

Embodiment 21m is the one or more food allergens at premeasured doses for use of any one of embodiments 21-21l, wherein the third food allergen is selected from the group consisting of cow milk, egg, peanut, wheat, soy, sesame, fish, shellfish, and tree nut.

Embodiment 21n is the one or more food allergens at premeasured doses for use of any one of embodiments 21-21m, wherein the third food allergen is peanut.

Embodiment 21o is the one or more food allergens at premeasured doses for use of any one of embodiments 21-21n, wherein the premeasured doses of the food allergens are mixed into breast milk, supplementation, or food prior to administering the allergens to the subject.

Embodiment 21p is the one or more food allergens at premeasured doses for use of any one of embodiments 21-21o, wherein the premeasured doses of the food allergens are in the form of powder.

Embodiment 21q is the one or more food allergens at premeasured doses for use of any one of embodiments 21-21p, wherein the food allergens consist of particles having a particle size of less than about 200 microns.

Embodiment 21r is the one or more food allergens at premeasured doses for use of any one of embodiments 21-21c, wherein the exposure dose of each food allergen is between about 0.01 and 0.3 grams and the maintenance dose of each food allergen is between about 0.05 and 1 grams.

Embodiment 21s is the one or more food allergens at premeasured doses for use of any one of embodiments 21-21r, wherein the first food allergen comprises cow milk and the exposure dose of the first food allergen is about 0.2 grams of cow milk proteins, wherein the maintenance dose of the first food allergen is about 0.4 grams of cow milk proteins.

Embodiment 21t is the one or more food allergens at premeasured doses for use of any one of embodiments 21-21s, wherein the second food allergen comprises egg and the exposure dose of the second food allergen is about 0.03 grams of the egg proteins, wherein the maintenance dose of second food allergen is about 0.1 grams of the egg proteins.

Embodiment 21o is the one or more food allergens at premeasured doses for use of any one of embodiments 21-21t, wherein the third food allergen comprises peanut and the exposure dose of the third food allergen is about 0.1 grams of the peanut proteins, and wherein the maintenance dose of third food allergen is about 0.4 grams of the peanut proteins.

Embodiment 22 is a kit or a combination containing at least two of:
(a) a first composition which comprises a skin barrier function composition;
(b) a second composition comprising an effective amount of a probiotic, such as a *Bifidobacterium* cell; and
(c) premeasured doses of one or more food allergens.

Embodiment 22a is the kit or combination of embodiment 22, wherein the kit or combination is for use in treating or reducing the onset or occurrence of childhood atopic disease in a subject in need thereof.

Embodiment 22b is the kit or combination of embodiment 22 or 22a, wherein the first combination is the first combination described in any one of embodiments 2-4d. Embodiment 22c is the kit or combination of any one of embodiments 22-22b, wherein the second combination is the second combination described in any one of embodiments 5-10b.

Embodiment 22d is the kit or combination of any one of embodiments 22-22c, wherein the food allergens are the food allergens described in any one of embodiments 11-18c.

Embodiment 23 is any one of the foregoing embodiments, wherein the probiotic includes, but is not limited to, a bacterial strain selected from *Lactobacillus, Lacticaseibacillus* and *Bifidobacterium* genera.

Embodiment 23 is any one of the foregoing embodiments, wherein the probiotic includes, but is not limited to, a bacterial strain of *B. infantis, B. Longum* (subspecies other than *B. infantis*), *B. Breve, B. catemulatum, B. adolescentis, B. animalis, B. gallicum, B. lactis, B. pseudocatemilatum, B. Bifidum, L. paracasei, L. acidophilus, L. johnsonii, L. delbrueckii, L. crispatus, L. gasser, L. zeae, L. casei, L. rhamnosus, Lactiplantibacillus plantarum, Limosilactobacillus fermentum, Ligilactobacillus salivarius*, or a combination thereof.

EXAMPLES

Example 1: STOP AD (Short-Term Topical Application for Prevention of Atopic Dermatitis), a Randomized, Open-Label, Controlled Clinical Trial This clinical trial study is designed to investigate the effect of short-term neonatal skin barrier protection using the skin treatment regimen and composition below on the prevention of atopic dermatitis in high-risk infants. (See clinicaltrials.gov/ct2/show/NCT03871998; ucc.ie/en/paediatrics/programmes/postgraduateprogrammes/phd-students/; and www.infantcentre.ie/research/research-studies/stop-ad/; and www.authorea.com/doi/full/10.22541/au.164940311.12725370/v1; and Ni Chaoimh, et al., Parental compliance with an infant moisturization protocol in the first 2 months of life; Lad et al., Can more be done to implement translational weaning advise for new mothers; and Lad et al., Neonatal natural moisturizing factor concentrations in a high-risk cohort with parental history of atopy compared to a reference cohort, each presented at European Academy of Allergy and Clinical Immunology (EAACI) 2020).

High-risk infants were identified using parental history of atopic disease and were randomized to either the skin treatment regimen and composition or standard routine care, each set forth below, from soon after recruitment in the postnatal ward (approximately 4 day) until eight weeks of age. Both the intervention and standard of care groups were advised to use a standardized bathing routine for the first 2 months.

Skin treatment regimen and composition: twice daily whole-body application of AVEENO® Dermexa Fast & Long-Lasting Balm, which on pack contains the following ingredients: glycerin, aqua, cetearyl alcohol, isocetyl alcohol, dimethicone, cetyl alcohol, *Avena sativa* kernel flour, *Avena sativa* kernel extract, *Avena sativa* kernel oil, caprylic/capric triglyceride, ceramide 3, ethylhexylglycerin, p-anisic acid, sodium cetearyl sulfate, palmitic acid, stearic acid, sodium sulfate, sodium chloride, citric acid, dipotassium phosphate, potassium phosphate, sodium hydroxide, tocopherol, benzyl alcohol, benzoic acid, and potassium sorbate.

Control: Standard routine care, which involves no use of moisturizer for the first two months.

Both groups received: AVEENO® Baby Daily Care Gentle Wash, which on pack contains the following ingredients: aqua, glycerin, cocamidopropyl betaine, sodium lauroamphoacetate, coco-glucoside, sodium chloride, hydroxypropyl starch phosphate, *Avena sativa* kernel flour, *Aloe barbadensis* leaf juice, *Olea europaea* leaf extract, *Chamomilla recutita* extract, *Helianthus annuus* seed oil, sarcosine, magnesium aspartate, potassium aspartate, polyquaternium-7, polysorbate 20, sodium cocoyl amino acids, acrylates/C10-30 alkyl acrylate crosspolymer, propylene glycol, citric acid, sodium hydroxide, tocopherol, tocopheryl acetate, sodium benzoate, potassium sorbate, sodium sulfite, parfum.

Infants with at least one parent with a positive history of atopic disease (AD, allergic rhinitis or asthma) were eligible for recruitment. Additional inclusion or exclusion criteria are set forth below.

Inclusion Criteria:
  Healthy full-term infants, gestational age >36+6 weeks.
  At least one parent with self-reported atopic dermatitis, food allergy, allergic rhinitis or asthma.
  Not require admission to the neonatal unit.

Exclusion Criteria:
  No parental history of atopic disease.
  Require admission to the neonatal unit for issues other than the establishment of normal feeding.
  Having been administered oral or parenteral antibiotics.
  Receiving phototherapy for hyperbilirubinaemia.
  Sibling, including twin, already recruited.
  Other serious health issues (e.g., abdominal wall defects, congenital heart disease etc.) or a severe widespread skin condition (e.g., collodion).
  Any condition that would make the use of skin barrier protectant inadvisable or not possible (e.g., ankle talipes or developmental dysplasia of the hip, requiring a Pavlik's harness or casts).
  Participation in any other clinical trial of an investigational medicinal product.

Within approximately 4 days of birth, infants were randomized to either treatment with skin treatment regimen and composition or to standard routine skincare with no moisturizer until 2 months of age. 260 infants participated in the study, including 120 in the intervention group and 140 in the control group.

The study had six visits during the first year of life, within 4 days of birth and at 2, 4 and 8 weeks and 6 and 12 months, involving repeat measurements of weight, trans-epidermal water loss (TEWL) and Raman-derived natural moisturizing factor (NMF) to assess skin barrier function and structure in addition to monitoring of skin health and feeding. A questionnaire on infant health, bathing, feeding and skincare was filled out and skin swabs were taken for microbiome and immune biomarker analysis.

The study's primary outcome was the effect of the intervention on the incidence of atopic dermatitis at 12 months. Secondary outcomes included the effect of the intervention on the incidence of atopic dermatitis at 6 months and the evolution of TEWL and NMF values from 0-12 months.

Skin swabs were taken at baseline and again at 8 weeks and at 12 months. A healthcare worker blind to treatment allocation assessed the presence (yes/no), extent and severity of atopic dermatitis at 6 and 12 months. A DNA sample was taken to test for filaggrin loss-of-function mutations, which are linked to atopic dermatitis risk.

I-SEAL (Insights towards understanding Skin Function in Early Life) involved the collection of skin microbiome and immunity biomarkers within the larger intervention trial STOP AD in order:
  to examine the temporal transition of the skin microbiome between birth and 12 months and its influence on the development of atopic dermatitis.
  to investigate the impact of the use of the skin regimen and composition in the first two months of life on infant skin microbiota.
  to investigate the dynamics of immunity biomarkers collected from the surface of infant skin in the first 12 months, and to examine associations with atopic dermatitis.

Results

Recruitment/Retention

A total of 3059 infants were screened for eligibility between April 2019 and November 2020, of whom 321 were randomised (161 to intervention and 160 to control). Baseline characteristics were balanced across the groups (Table 1). There were 61 withdrawals (41 intervention and 20 control, 19% attrition), with the majority (80%) occurring before the 2 week visit. The mean (SD) age at randomization was 1.9 (0.9) days.

TABLE 1

Baseline characteristics

|  | Intervention (n = 161) | Control (n = 160) |
|---|---|---|
| Maternal characteristics | | |
| Age [mean (SD) years] | 33.3 (4.4) | 34.1 (4.8) |
| Country of birth (Ireland) | 142 (88.2) | 139 (86.9) |
| Ethnicity (white) | 156 (96.9) | 158 (98.8) |
| Paternal characteristics | | |
| Age [mean (SD) years] | 35.3 (5.7) | 35.9 (5.5) |
| Country of birth (Ireland) | 142 (88.2) | 143 (89.4) |
| Ethnicity (white) | 157 (97.5) | 159 (99.4) |
| Infant characteristics | | |
| Sex (male) | 79 (49.1) | 85 (53.1) |
| Gestational age [mean (SD) weeks] | 39.7 (1.1) | 39.5 (1.1) |
| Birth weight [mean (SD) kg] | 3.6 (0.4) | 3.6 (0.5) |
| Mode of delivery | | |
| Vaginal | 98 (61.3) | 103 (64.4) |
| Caesarean section | 62 (38.8) | 57 (35.6) |
| Age randomised [mean (SD) days] | 1.9 (1.0) | 1.8 (0.8) |
| Baseline TEWL [median (IQR) gwater/m2/h] | 9.31 (7.25, 12.41) | 9.25 (7.44, 13.31) |
| Baseline NMF [median (IQR) g/g protein] | 0.32 (0.22, 0.42) | 0.33 (0.25, 0.41) |
| Family history of atopy | | |
| Maternal atopy | | |
| Allergic rhinitis | 81 (50.3) | 63 (39.4) |
| Atopic dermatitis | 40 (24.8) | 56 (35.0) |
| Asthma | 54 (33.5) | 63 (39.4) |
| Any maternal atopy | 112 (69.6) | 107 (67.3) |
| Paternal allergy | | |
| Allergic rhinitis | 66 (41.8) | 75 (47.2) |
| Atopic dermatitis | 43 (27.2) | 45 (28.3) |
| Asthma | 56 (35.4) | 53 (33.3) |

TABLE 1-continued

Baseline characteristics

|  | Intervention (n = 161) | Control (n = 160) |
|---|---|---|
| Any paternal atopy | 101 (63.9) | 107 (67.3) |
| Two parents with atopic history | 52 (32.9) | 54 (34.2) |
| Participant with at least one sibling | 87 (54.0) | 94 (58.8) |
| Of which, at least one sibling with | | |
| Allergic rhinitis | 20 (23.0) | 21 (22.3) |
| Atopic dermatitis | 35 (40.2) | 41 (43.6) |
| Asthma | 12 (13.8) | 13 (13.8) |

TABLE 1-continued

Baseline characteristics

|  | Intervention (n = 161) | Control (n = 160) |
|---|---|---|
| FLG genotyping | | |
| FLG wildtype | 96/117 (82.1) | 113/136 (83.1) |
| FLG null mutation (one) | 21/117 (17.9) | 22/136 (16.2) |
| FLG null mutation (two) | 0 | 1/136 (0.7) |

Data are n (%) unless stated otherwise.
Abbreviations:
TEWL = Transepidermal water loss,
NMF = Natural mositurising factor,
FLG = gene encoding filaggrin Protocol Adherence In the questionnaires, most parents in the IG reported applying emollient at least once daily in the first 8 weeks; 2 weeks: 89%, 4 weeks: 91.7%, 8 weeks: 86.6% (Table 2). Twice-daily application was reported by 63.3% at 2 weeks, 69.2% at 4 weeks and 73.1% at 8 weeks. Of those in the IG with questionnaires at all three time-points (n=114), 89 (78.1%) reported daily emollient use at all three time-points. Less than 20% of the CG reported emollient use on ≥4 days per week at any of the time-points; 19% at 2 weeks, 17.5% at 4 weeks and 13.5% at 8 weeks. Of those in the CG with questionnaires at all time-points (n=132), 90 (68.2%) reported using emollients on <4 days per week at all three time-points. There was no significant difference in bathing frequency between the groups over the intervention period.

TABLE 2

Parent-reported emollient application frequency at 2, 4 and 8 weeks (questionnaire data)

|  | Intervention (n = 120) 2 weeks (n = 118) | Intervention (n = 120) 4 weeks (n = 120) | Intervention (n= 120) 8 weeks (n = 119) | Control (n = 140) 2 weeks (n = 137) | Control (n = 140) 4 weeks (n = 137) | Control (n = 140) 8 weeks (n = 140) |
|---|---|---|---|---|---|---|
| Never | 0 | 0 | 0 | 47 (34.3) | 39 (28.5) | 34 (24.1) |
| Occasionally | 1 (0.8) | 0 | 0 | 25 (18.2) | 25 (18.2) | 25 (17.7) |
| Once/week | 1 (0.8) | 0 | 2 (1.7) | 7 (5.1) | 9 (6.6) | 10 (13.5) |
| 2-3/week | 3 (2.5) | 3 (2.5) | 5 (4.2) | 32 (23.4) | 40 (29.2) | 44 (31.2) |
| 4-6/week | 8 (6.8) | 6 (5.0) | 9 (7.6) | 16 (11.7) | 17 (12.4) | 11 (7.8) |
| Daily | 105 (89.0) | 111 (91.7) | 103 (86.6) | 10 (7.3) | 7 (5.1) | 8 (5.7) |
| Twice/day | 75 (63.6) | 83 (69.2) | 87 (73.1) | 2 (1.5) | 0 | 0 |

Data are n (%)

Diaries measuring adherence were returned by 95% (114/120) of the IG and 82.1% (115/140) of the CG. The mean (SD) age that emollient use started in the IG was 3.5 (1.5) days and 41.2% (47/114) reported that they applied emollient at least once on ≥90% of recording days (>6 days/week). A further 41.2% (47/114) reported emollient use for ≥75% of recording days (>5 days/week). Eighty percent (92/115) of the CG applied an emollient on ≤43% of the recording days (≤3 days a week).

There was no significant difference in the prevalence of regular emollient use (>4 days a week) between the groups at 6 and 12 months (intervention vs. control: 29.6% vs 29.7%, p=1.000 at 6 months and 28.4% vs. 25.8%, p=0.868 at 12 months).

Safety

No family sought emergency medical assessment related to the study intervention. Parent-reported skin infections during the 8-week intervention period occurred in 5% (6/120) of the IG and 5.7% (8/140) of the CG. One IG infant was advised to stop applying the emollient after developing a rash that had a potential temporal relationship with the emollient and was withdrawn from the study. Two suspected reactions to the study emollient were investigated and confirmed as having no relationship.

Primary Outcome

The cumulative incidence of AD at 12 months was 32.8% in the IG vs. 46.4% in the CG, p=0.036 [Relative risk (RR) (95% CI): 0.707 (0.516, 0.965)]. The point prevalence of AD at 12 months, where the child met the UKWPDC at the assessment, was 20.5% in the IG vs. 38.2% in the IG, p=0.003 [RR (95% CI): 0.536 (0.354, 0.813)].

Secondary AD Outcome

The cumulative incidence of AD at 6 months was 18.3% in the IG vs. 36.4% in the CG, p=0.002 [RR (95% CI): 0.503 (0.325, 0.779)]. The point prevalence at 6 months was 18.3% in the IG and 35.0% in the CG, p=0.004 [RR (95% CI): 0.524 (0.337, 0813)], Table 3.

TABLE 3

Atopic dermatitis outcomes at 6 and 12 months

|  | Total | Intervention | Control | P-value | Relative Risk (95% CI) |
|---|---|---|---|---|---|
| Primary outcome | | | | | |
| Cumulative AD at 12 months | 103/257 (40.1%) | 39/119 (32.8%) | 64/138 (46.4%) | 0.036 | 0.707 (0.516, 0.967) |
| Secondary outcomes AD at 12 months | | | | | |
| AD according to the UK Working Party Diagnostic Criteria[†] | 76/253 (30%) | 24/117 (20.5%) | 52/136 (38.2%) | 0.003 | 0.536 (0.354, 0.813) |
| AD at 6 months | | | | | |
| AD according to the UK Working Party Diagnostic Criteria[†] | 71/260 (27.3%) | 22/120 (18.3%) | 49/140 (35.0%) | 0.004 | 0.524 (0.337, 0.813) |
| Cumulative AD | 73/260 (28.1%) | 22/120 (18.3%) | 51/140 (36.4%) | 0.002 | 0.503 (0.325, 0.779) |

[†]Point prevealance.
Abbreviations:
AD = atopic dermatitis

Time-to-event survival analysis using the Kaplan-Meier method demonstrates that the IG maintained AD-free skin for a longer period in the first 12 months than the CG (=0.016, log-rank test, FIG. 3). Of those with AD outcome data at 6 and 12 months (n=117 intervention, n=137 control), 7.7% of IG and 8.0% of CG infants were diagnosed at ≤6 months, but no longer met the criteria at 12 months (p=1.0). The prevalence of AD onset between 6 and 12 months was 13.7% and 9.5% in the IG and CG, respectively (p=0.397) and 10.3% vs. 29.2% met the criteria at both 6 and 12 months (p<0.001), (See Supplementary FIG. 1). SCORADs were completed for those ≥6 months at diagnosis (n=55). There was no significant difference in SCORAD total scores at diagnosis between the groups [median (IQR) SCORAD: IG 11.3 (8.0, 18.4), vs. CG 12.3 (7.4, 16.0), p=0.888].

A similar, but non-significant relative risk was observed for the primary outcome in the per-protocol analyses [Questionnaire per-protocol analysis RR (95%) CI: 0.713 (0.501, 1.014), P=0.078); Diary per-protocol analysis RR (95% CI): 0.745 (0.474, 1.173), P=0.253].

Food Allergen Sensitization

All infants had been introduced to dairy and almost all had been introduced to egg (99.6%) and peanut (98.0%) by 12 months. Nine infants had a positive SPT to at least one food [intervention; 3.3% (4/120), control; 3.6% (5/120), p=1.0].

TEWL and NMF Evolution

There were no significant differences in TEWL or Thenar NMF between the intervention and control groups at birth, 2, 4, 8 weeks or at 6 and 12 months.

Discussion

In this RCT in high-risk infants, it was found that daily emollient use initiated in the first week of life until 2 months is associated with a significant reduction in the cumulative incidence of AD at 12 months. Daily emollient use was associated with a 50% and 29% reduction in the risk of the cumulative incidence of AD at 6 and 12 months, respectively. Similar risk reductions were observed in the per-protocol analyses where only those in the intervention and control groups were included if they used emollients at least once daily and <4 days a week, respectively. However, these were not significant for the primary outcome which may be due to the conservative adherence criteria applied and thus, lower numbers included in the analysis and therefore lower power to detect differences between the groups.

While some AD cases diagnosed before 6 months had resolved by 12 months, there was no difference in transient cases between the groups. As we did not collect longer term data, we cannot exclude the possibility that the intervention may have only delayed the onset of AD beyond 12 months. A recent meta-analysis reported a protective effect of emollients but only when there was no interval between the emollient treatment and AD assessment 14. However, there was significant heterogeneity between the four studies included in that analysis. In our study, a 29% reduction in the risk of cumulative AD at 12 months, was maintained 10 months after the intervention.

The findings are at variance with recent findings from two large RCTs, where no evidence of a protective effect of emollient use in the first year against A D was found (Chalmers J R, Haines R H, Bradshaw L E, et al, "Daily emollient during infancy for prevention of eczema: the BEEP randomised controlled trial," Lancet Lond. Engl., 2020, 395 (10228):962-972; Skjerven H O, Rehbinder E M, Vettukattil R, et al., "Skin emollient and early complementary feeding to prevent infant atopic dermatitis (PreventADALL): a factorial, multicentre, cluster-randomised trial," Lancet Lond. Engl., 2020, 395 (10228):951-961). Among the most notable differences between these RCTs and ours was the timing of the intervention. The treatment in STOP AD began within days of birth during a dynamic period of skin maturation and adaption to the dramatic environmental changes of life ex utero. In STOP AD, infants were randomised within 4 days of birth with the IG advised to begin the emollient treatment immediately. In BEEP, the median (IQR) age that emollient use began was 11 days (7, 17) days, with only 89% starting emollient application before 3 weeks. In PreventADALL, the intervention began from 2 weeks of age.

The emollients used in BEEP and PreventADALL were basic petroleum and paraffin-based formulations, respectively. The emollient used in this study consists of a formulation with added ceramides developed specifically for very dry itchy skin. Two small studies that also used more complex ceramide-rich emollients reported non-significant trends towards a protective effect against AD (Lowe A J, Su J C, Allen K J, et al. "A randomized trial of a barrier lipid replacement strategy for the prevention of atopic dermatitis and allergic sensitization: the PEBBLES pilot study," Br. J. Dermatol., 2018, 178(1): e19-e21; McClanahan D, Wong A, Kezic S, et al. "A randomized controlled trial of an emollient with ceramide and filaggrin-associated amino acids for the primary prevention of atopic dermatitis in high-risk infants," J. Eur. Acad. Dermatol. Venereol., 2019, 33(11):2087-2094). Following one of these, a larger scale RCT, the PEBBLES study, involving twice-daily application of the same ceramide-based emollient from 0-6 months is ongoing25. Here we showed a reduced risk of AD at 12 months with a short 2-month intervention period, which may represent a more feasible and family friendly strategy for AD prevention.

Our high adherence rates demonstrate the feasibility of implementing a regimen of daily emollient use during the first 2 months of life. Adherence rates using the diaries were lower than reported on the questionnaires but 82.4% still reported using emollients on >75% of days equating to over 5 days a week. While infants in this study were followed closely during the intervention period, similar rates of adherence were observed in BEEP which involved limited contact, but used a less strict definition for adherence (emollient use >3 days/week)10. Only 27% of the IG fully adhered to the protocol in PreventADALL which may have influenced the absence of a protective effect.

While we did assess food allergy outcomes, this study was not powered to detect a reduction in food allergy risk. Unlike BEEP, where a non-significant increase in food allergy in the IG has been prominently reported, we found no difference in the prevalence of food allergy between the groups. While we did not use SPTs to screen for food allergy, almost all infants had tried the most common food allergens—milk, egg and peanut—by 12 months, so the rate of food sensitization and allergy reported is likely reflective of the true rate in our groups. BEEP reported a higher rate of skin infections in the IG, with suggestions of the possibility of greater pathogen exposure with emollient application. We did not find evidence of an increased risk of skin infections with short-term emollient use.

Despite the reduction of AD risk in the IG, there was no difference in TEWL throughout the first year between the groups. Other studies on emollient use during infancy reported a similar absence of an effect of the intervention on TEWL. TEWL measurements are influenced by environmental factors and more crucially for infants, subject-specific parameters including stress and crying26. This may have affected our ability to detect differences between the groups.

The major strength of this study is the initiation of emollient use within days of birth in the IG. Other strengths include the close follow-up of infants, a high rate of adherence in the IG and a low rate of contamination in the CG.

A limitation to this study is that in response to the COVID-19 pandemic, many AD diagnoses were made remotely. To mitigate this, detailed information and photographs were collected when making a diagnosis. SCORAD assessments were also completed remotely, which may have affected assessments of AD severity. Validated diagnostic criteria could not be applied when diagnosing earlier onset AD (<6 months), where cases were diagnosed based on presence of AD lesions. However, of the 73 infants diagnosed with AD ≤6 months, 71 (97.3%) met the UKWPDC at 6 months. The prevalence of cumulative AD in this group was higher than expected based on the rates among infants with parental history of atopy in an Irish birth cohort 23. A possible explanation for this is the a priori recruitment of high-risk infants and the close monitoring of skin health in this study. Only a third (32.1%) of those eligible for this study were recruited. One of the main reasons for the refusal to participate was the demanding follow-up schedule involved, particularly during the intervention period that started before going home with their newborn baby, suggesting that more motivated individuals were recruited. We also had a higher rate of withdrawals in the first two weeks of life, particularly in the intervention group, mainly due to withdrawal of consent and not due to early onset of AD by this time. This is a consideration in assessing the feasibility of advising daily emollient use in the early postnatal period to a more general population.

We have demonstrated that early initiation of daily specialized emollient use until 2 months reduces the incidence of AD in the first year of life in high-risk infants. The mechanisms behind this are unclear but analysis of microbiome diversity and inflammatory biomarkers in a subgroup of this study is ongoing and may provide further information. While several recent studies do not support a protective effect of emollient use in infancy, future studies should examine the use of more complex emollients directed at enhancing the skin barrier, while identifying a treatment window that is both effective and acceptable to parents.

Example 2: BACH Clinical Trial, a Study on Clinical and Immunological Effects of *B. infantis* (Strain EVC001; Evolve BioSystems, Inc., Davis, CA) Supplementation This clinical trial study is a randomized, placebo-controlled experimental study aimed to decrease or eliminate known confounding effects from factors other than the study intervention (Clinical Trials.gov Identifier: NCT04662619). This type of study design is thus considered to be rigorous because it is able to test causal relationships between the study intervention (in this case, the Study Supplement) and study endpoints.

Objectives

The primary objective of this study is to assess the effect of *B. infantis* (EVC001) versus placebo supplementation, in healthy breastfed infants at risk of developing AD, on the cumulative incidence of physician-diagnosed AD during the first year of life. The secondary objective of this study is to assess the effect of *B. infantis* (EVC001) versus placebo supplementation, in healthy breastfed infants at risk of developing AD, on:
  The proportion of infants with adverse events (AEs) in order to evaluate safety and tolerability
  The cumulative incidence of AD at additional timepoints
  The time to onset of AD
  *B. infantis* colonization of the infant gut
  AD severity for subjects with
  AD Additional objectives of this study are:
  1) To assess the effect of *B. infantis* (EVC001) versus placebo supplementation, in healthy breastfed infants at risk of developing AD, on:
  Incidences of atopic disease other than AD (food allergy, allergic rhinitis, asthma)
  Allergic sensitization
  Gut and skin microbiome
  Skin immunological biomarker profile Incidence of infantile colic
Infant sleep
Infant anthropometrics
Relationship between baseline maternal gut microbiome and the development of the infant gut microbiome 2) To characterize and compare microbiome and immunological profiles between infants who do not develop AD through 1 year and infants who do in the *B. infantis* (EVC001) supplementation group and in the placebo supplementation group.

3) To determine the immune responder phenotype in the *B. infantis* (EVC001) supplementation group and in the placebo supplementation group.

4) To identify the subject genetic profile linked to benefit from the supplement intervention.

Overview

This study is a randomized, double-blind, placebo-controlled, 2-arm, parallel-group (Groups 1 and 2) study. The study will enroll approximately 286 infants with at least one first-degree relative having a history of atopic disease (i.e., biological parent or full sibling with mother-reported, physician-diagnosed AD, allergic rhinitis, or asthma) who are currently breastfed, with maternal intent to maintain exclusive breastfeeding for at least 12 weeks (approximately 3 months). Each infant will participate in the study under the supervision of his/her biological mother ("Caregiver").

Infant eligibility evaluations will be conducted within the first 14 days of life. Eligible infants will be enrolled and randomized evenly (1:1) to one of two groups: placebo (Group 1) or *B. infantis* (EVC001) (Group 2). The randomization will be stratified by the number of the infants' first-degree relatives (one versus more than one) having a history of relevant atopic disease (as defined above). All baseline assessments will be conducted prior to the first administration of the assigned Study Supplement.

Administration of the assigned Study Supplement will commence on Day 0 and continue for 12 weeks. Caregiver will be instructed to make their best effort to maintain exclusive breastfeeding for at least this 12-week period, and they will be encouraged to continue breastfeeding for as long as possible during the first year of life. Following the 12-week Supplementation Period, infants will be followed through Week 104 (approximately 2 years) via scheduled and unscheduled visits.

A sub-study is planned with a subset of the main study population (approximately 80-100 subjects) to evaluate the possible relationships between the intestinal microbiome, frequency, and function of specific immune cells in the peripheral circulation, the circulating cytokine profile, and the development of AD.

Subject Selection and Enrollment

The eligibility criteria are designed to select subjects for whom protocol procedures are considered appropriate. Infant eligibility will be assessed within the first 14 days of the newborn's life. The initial verification of eligibility may be conducted by a non-medically qualified individual.

The inclusion criteria of the infant includes the following:
1) Male or female newborn ≤14 days old at the time of study enrollment (Day 0).
2) Healthy term infant.
3) Has at least one first degree relative (i.e. biological parent or full sibling) with history of atopic disease (i.e., mother-reported, physician-diagnosed AD, allergic rhinitis, or asthma).
4) Breastfeeding established at the time of study enrollment (Day 0), with maternal intent to maintain exclusive breastfeeding for ≥12 weeks.

The exclusion criteria of the infant includes the following:
1) Preterm delivery (<36 weeks [252 days] gestational age).
2) Admission to the neonatal unit for issues other than establishment of normal feeding.
3) Evidence of a baseline illness/condition (e.g. abnormal birth weight) or significant risk of developing an illness/condition (based on review of maternal/pregnancy information) that would, in the opinion of the PI or designee, introduce a significant safety concern if the infant were enrolled in the study or otherwise preclude study participation.
4) Significant birth defect/complication that would, in the opinion of the PI or designee, create a safety concern or otherwise confound the study (e.g., abdominal wall defects, congenital heart disease).
5) Severe widespread skin condition (e.g., collodion).
6) Medical condition (infant) or maternal medication/supplement use (e.g., daily or routine antibiotics or systemic antifungals) that, in the opinion of the PI or designee, may significantly alter the gut or skin microbiome.
7) Has consumed a prebiotic or (a) *Bifidobacterium longum*-containing probiotic supplement/milk/formula prior to enrollment (Day 0).
8) Has consumed >100 mL of formula per day within the 48 hours prior to enrollment (Day 0).
9) Medical condition (infant) or maternal surgery/injury/condition that would preclude breastfeeding.
10) Known infant sensitivity to, or intolerance of, soya or dairy protein consumption.
11) Maternal infection with human immunodeficiency virus, tuberculosis, hepatitis C, or hepatitis B.
12) Caregiver condition that, in the opinion of the PI or designee, would not allow the Caregiver and/or infant to comply with the study protocol requirements.
13) Twin or multiple births.

During the study, the infant's Caregiver will be directed to make their best effort to ensure the infant is exclusively fed breast milk through at least Week 12, and encouraged to continue breastfeeding for as long as possible during the first year of life. The Caregiver will also administer the assigned Study Supplement to the infant once daily for 12 weeks according to provided instructions and training. The Caregiver will be instructed to avoid routine infant ingestion of probiotics for the first 12 weeks of the study (or during the breastfeeding period, if longer), unless specifically prescribed by an HCP, e.g., to prevent or treat antibiotic-associated diarrhea or treat gastroenteritis. The Caregiver will also be directed to ensure that the infant does not ingest any prebiotics or any *Bifidobacterium*-containing probiotic supplement/milk/formula during the first 24 weeks of the study.

Sample Size, Randomization/Study Supplement Allocation and Blinding

Approximately 200-400 subjects will be randomly assigned in a 1:1 ratio to receive *B. infantis* (EVC001) or placebo. Enrolled infants will be randomized evenly (1:1) to the active or placebo supplementation arm according to a randomization schedule. Infants will be stratified by the number of first-degree relatives (one versus more than one) having a history of atopic. The study will be double-blinded, so that the Caregivers and the PI/designees do not know the Study Supplement assignment.

Identity and Use of Study Supplements

The following Study Supplements will be provided, as shown in Table 4 below:

TABLE 4

Study Supplements

| Identification | Product type |
| --- | --- |
| B. infantis (EVC001) | Active supplement |
| Matching lactose placebo | Placebo supplement |

The active supplement is B. infantis supplement Evivo® probiotic powder available from Evolve BioSystems, Inc. in sachets and having ingredients: purified lactose, B. longum subsp. infantis EVC001 per dose. Each sachet contains 625 mg of the probiotic powder and contains 8 billion CFU of B. infantis (EVC001). The placebo sachets contain 625 mg of lactose.

Infants will ingest the contents of a single-serving sachet of B. infantis (EVC001) or matching placebo Study Supplement once daily for 12 weeks. At the time of supplementation, the contents of a single-serving sachet will be mixed with approximately 3-5 mL of expressed or pumped breast milk (or infant formula, if needed) in a provided reservoir. Using the provided syringe, the mixture will be dispensed into the side of the infant's mouth to ensure the infant ingests the entire dose.

Study Duration, Procedures and Evaluation Schedule

Infant eligibility evaluations will be conducted within the first 14 days of the infant's life. Following enrollment and randomization (Day 0), the Study Supplement will be administered daily from Day 0 through Week 12. Caregivers will be instructed to make their best effort to maintain exclusive breastfeeding for ≥12 weeks. Following the 12-week Supplementation Period, study subjects will be followed for an additional 92 weeks to complete this 104-week (2-year) study.

Assessment Tools and Additional Study Procedure Details

Medical, Family, Medication, and Supplement History Questionnaire:

At Screening, Study Personnel will interview each infant's Caregiver to complete the Medical, Family, Medication, and Supplement History Questionnaire to document the infant's medical history and medication/supplement history, including exposures during/from pregnancy, birth, and breastfeeding. The questionnaire will also capture mother-reported information about the infant's first degree relatives having a history of atopic disease, for example current or prior history of AD (including age of onset and details of diagnostic testing), allergic rhinitis/hay fever (including identification of allergens), asthma, food reaction/allergy (such as type of food and reaction; details of any other formal allergy testing), other skin conditions, or an immune-mediated disease.

Diagnosis of AD:

Infants with possible cases of AD identified by Study Personnel will be assessed by a trained physician for evaluation and diagnosis. Briefly, AD will be diagnosed if three of the following four criteria are met: 1) pruritus, 2) typical morphology and distribution (facial and extensor involvement), 3) chronic or chronically relapsing dermatitis, 4) personal or family history of atopic disease (Rajka G, Langeland T. Grading of the severity of atopic dermatitis. Acta Derm Venereol Suppl (Stockh) 1989; 144:13-4.; Gånemo A, Svensson Å, Svedman C, Grönberg BM, Johansson AC, Wahlgren CF. Usefulness of Rajka & Langeland Eczema Severity Score in clinical practice. Acta Derm Venereol 2016; 96:521-4.).

If the infant is diagnosed with AD, the EASI and POEM, described below, will be employed to assess its severity at the time of diagnosis and at Weeks 12, 52, and 104.

Eczema Area and Severity Index (EASI) 8 Years of Age:

The EASI is a tool used to measure the extent (area) and severity of atopic eczema/AD (Hanifin JM, Thurston M, Omoto M, Cherill R, Tofte SJ, Graeber M. The eczema area and severity index (EASI): assessment of reliability in atopic dermatitis. EASI Evaluator Group. Exp Dermatol 2001; 10:11-8.). The instrument assesses four body regions: the head and neck (including face, neck, and scalp), trunk (including genital area), upper limbs (including hands), and lower limbs (including buttocks and feet), which are assigned proportionate body surface areas of 20%, 30%, 20%, and 30%, respectively. An area score is determined for each of these four body regions based on the percentage of skin affected by AD (as defined by the four key signs listed below) within that body region (0=None, 1=1-9%, 2=10-29%, 3=30-49%, 4=50-69%, 5=70-89%, 6=90-100%). Each of the four body regions is also assessed for the severity of four key signs of AD—erythema, induration/papulation/edema, excoriation, and lichenification—using a 0 to 3 scale: 0=none; 1=mild; 2=moderate; and 3=severe (note: half-points are allowed). The total score for each body region is determined by multiplying the sum of the severity scores of the four key signs by the area score, then multiplying the result by the constant body surface area assigned to that body region. The total EASI score is the sum of the body region scores and ranges from 0 to 72. A trained physician designated will assess AD severity using the EASI at time of AD diagnosis and (only for subjects with AD) at Weeks 12, 52, and 104.

Patient-Oriented Eczema Measure (POEM):

The POEM is a simple, valid, easily interpreted, and reproducible tool for assessing AD and monitoring aspects of the disease that are important to patients (Charman CR, Venn AJ, Williams HC. The Patient-Oriented Eczema Measure: Development and initial validation of a new tool for measuring atopic eczema severity from the patients' perspective. Arch Dermatol 2004; 140:1513-9.; Charman CR, Venn AJ, Ravenscroft JC, Williams HC. Translating Patient-Oriented Eczema Measure (POEM) scores into clinical practice by suggesting severity strata derived using anchor-based methods. Br J Dermatol 2013; 169:1326-32.). Study Personnel will interview Caregivers at time of AD diagnosis and (only for subjects with AD) at Weeks 12, 52, and 104 to rate seven symptoms (itchy skin, sleep disturbance, bleeding skin, skin weeping/oozing, skin flaking, skin cracking, skin dryness/roughness) using a 5-point scale of frequency of occurrence during the previous week (no days, 1-2 days, 3-4 days, 5-6 days, every day). The maximum total POEM score is Infantile Colic Study Personnel will interview Caregivers to document signs and symptoms of infantile colic at Baseline (Day 0) and at Weeks 6, 12, and 24 based on the Rome IV criteria (Benninga M, Nurko S, Faure C, Hyman P, St. James-Roberts I, Schechter N. Childhood functional gastrointestinal disorders: neonate/toddler. Gastroenterology 2016; 150: 1443-55). As defined by the Rome IV criteria, the occurrence of infantile colic will be determined utilizing these Caregiver interviews in combination with daily Caregiver entries in a diary. Caregivers will utilize the diary to document the occurrence and duration of crying, fussing, and other related symptoms such as bowel movements at Baseline and daily during Weeks 5-7, 11-13, and 23-24. "Fussing" will refer to intermittent distressed vocalization and has been defined as "[behavior] that is not quite crying but not awake and content either" (Benninga, 2016; Zeevenhooven J, Koppen IJ, Benninga MA. The new Rome IV criteria for functional gastrointestinal disorders in infants and toddlers. Pediatr Gastroenterol Hepatol Nutr 2017; 20:1-13). As defined by the Rome IV criteria, the occurrence of infantile colic will be determined utilizing Caregiver diary entries in combination with the Caregiver interviews conducted at the visits.

Infant Anthropometrics

Infants will have their length/height (using an infant length board), body weight, and head circumference measured during all study visits. The Body Mass Index (BMI) will be calculated based on measurements of body weight and body length/height according to the following equation: BMI $(kg/m^2)$ =weight (kg)/([length or height in $cm/100]^2$).

Brief Infant Sleep Questionnaire—Revised (BISQ-R)

At Weeks 12, 24, 52, and 76, Caregivers will document the infant's sleep routines and patterns during the previous 2 weeks using the BISQ-R. The BISQ-R is an age-based, norm-referenced scoring system that provides a comprehensive assessment of infant and toddler sleep patterns (5 items related to sleep onset latency, number and duration of night wakings, longest stretch of sleep, and total night sleep), as well as parent perception (3 items related to bedtime difficulty, overnight sleep, overall child sleep problems) and parent behaviors (11 items related to bedtime routine consistency, bedtime, parental behavior at time of sleep onset and following night wakings, and sleep locations at time of sleep onset and following night wakings) that may impact sleep outcomes (Mindell JA, Gould RA, Tikotzy L, Leichman ES, Walters RM. Norm-referenced scoring system for the Brief Infant Sleep Questionnaire—Revised (BISQ-R). Sleep Med 2019; 63:106-14.). A score ranging from 0-100 is derived for each sub-scale, with higher scores denoting better sleep quality, more positive perceptions of sleep quality, and parental habits that promote healthy sleep behaviors and independent infant sleep, respectively. A total score is calculated as the average of the infant sleep, parent perceptions, and parent behavior subscale scores.

Solid Food Introduction Checklist

Caregivers will document the first time the infant ingests a new solid food, to include the type and amount of the solid food, as applicable.

Infant Feeding and Study Supplement Usage Log

Caregivers will record details of maternal breastfeeding, infant formula use (if applicable), and administration of the Study Supplement in a diary on a daily basis through Week 12 and optionally thereafter. Caregivers will also document any missed, incomplete, or extra administrations of the Study Supplement in the diary; missed supplementations will not be replaced on subsequent days.

Blood Samples

A 2.0 mL venous whole blood sample will be collected from infants at Weeks 24, 52, and 104. The blood will be processed and archived according to instructions provided in the Laboratory Reference Manual for future analyses. Allergen-specific serum IgE tests will be conducted using the venous whole blood samples to evaluate the development of allergic sensitization. In addition, the blood samples may also be used to investigate the infant immune responder phenotype by comparing serial RNA expression profiles of subjects in the B. infantis (EVC001) supplementation group and in the placebo supplementation group. The blood samples may also be used for exome-sequencing to determine the presence of variations in different genes, including the FLG gene, that might relate to atopic disease (e.g. AD, asthma, and allergic sensitization) and ichthyosis vulgaris.

Stool Samples

Maternal stool samples for future microbiome analysis will be collected 2-6 weeks postpartum, if the mother has consented to the collection (optional). Caregivers will collect infants' stool within 5 days (preferably within 3 days) prior to the Baseline (Day 0) and Weeks 6, 12, 24, 52, and 104 visits. The Baseline sample should be a non-meconium sample; if this is not possible prior to the start of supplementation, a deviation should be recorded and a non-meconium sample should be collected as soon as possible once supplementation has begun (preferably within 24 hours).

All stool samples will be collected using the provided supplies and stored frozen within a provided collection tube and biohazard bag until collected by Study Personnel during an in-person visit. Soft-sided coolers fitted with ice packs will be utilized to transport frozen stool samples to the Study Site where they will be stored at −80° C. for future analyses.

Stool collected at Baseline (Day 0) and Weeks 6, 12, 24, 52, and 104 will be analyzed for the overall bacterial profile of the gut including the presence of B. infantis to determine the extent (percentage of B. infantis colonization within each infant) and incidence (percentage of infants with gut B. infantis colonization) of colonization. An infant's gut will be considered colonized if the fecal concentration of B. infantis, determined by shotgun sequencing, is ≥50% of the total bacteria.

Skin Swab Samples

Caregivers will be instructed to avoid applying any topical treatment within 3 hours prior to a study visit so as not to interfere with collection of skin samples. All skin samples, collected as detailed below, will be stored frozen at −80° C. at the Study Site for future analysis, as detailed in the Laboratory Reference Manual.

Skin biomarkers: To assess the effects of B. infantis (EVC001) supplementation on immune regulation in the skin and to learn about biomarkers associated with the onset of AD, Study Personnel will collect two skin samples using FibroTX Skin Sample Collection Swabs at Baseline (Day 0), Week 12, and Week 52; if AD is diagnosed, two additional samples will be collected from lesional and adjacent clear nonlesional locations at these timepoints. The FibroTX Skin Sample Collection Swab is a highly sensitive multi-analyte research tool for noninvasive biomarker measurements directly from skin.

Skin microbiome: To assess the systemic effects of the Study Supplement on the skin's microbiome, Study Personnel will utilize pre-moistened swabs to collect two skin samples at Baseline (Day 0), Week 6, Week 12, and Week 52, one from the antecubital fossa (elbow crease) and the other at a location determined by Study Personnel or Sponsor. If AD is confirmed, two additional samples will be obtained from lesional skin and adjacent clear non-lesional skin at these timepoints.

Study Visits and Evaluations

A summary of the study procedures and evaluation schedule is shown in below in Table 5.

TABLE 5

Schedule of Events

| Study Period | Screening | Supplementation Period | | | | | Follow-up Period | | | |
|---|---|---|---|---|---|---|---|---|---|---|
| Study Visit[a, b] Additional definitions | Within 14 days postpartum[c] | Day 0 Baseline[d] | Week 6 | Week 12 (~3 months) EOS | Week 24 | Week 52 (~1 year) | Week 76 | Week 104 (~2 years) | Early D/C D/C[e] | Unscheduled Study Visit |

Administrative/Eligibility

| | | | | | | | | | | |
|---|---|---|---|---|---|---|---|---|---|---|
| ICD (and sub-study addendum, if applicable) (see Section 4.1) | X | | | | | | | | | |
| Demographic Questionnaire | X | | | | | | | | | |
| Medical, Family, Medication, and Supplement History Questionnaire | X | | | | | | | | | |
| initial inclusion/ exclusion criteria review[f] | X | | | | | | | | | |
| Final inclusion/ exclusion criteria review | | X | | | | | | | | |
| Caregiver provided with instructions and supplies for subsequent stool sample collection(s)[g] | X | X | X | X | X | | X | | | |

Randomization and Study Supplement

| | | | | | | | | | | |
|---|---|---|---|---|---|---|---|---|---|---|
| Enrollment/ randomization | | X | | | | | | | | |
| Caregiver training on Study Supplement administration and infant skin monitoring | | X | | | | | | | | |
| eDiary installation, registration, and training | | X | | | | | | | | |
| Dispense Study Supplement | | X | | | | | | | | |
| Administer Study Supplement | | | Once daily | | | | | | | |
| Final Study Supplement accountability | | | | X | | | | | X[h] | |

Study Assessments/Ongoing Review
Conducted by Study Personnel

| | | | | | | | | | | |
|---|---|---|---|---|---|---|---|---|---|---|
| Lactation support for Caregivers[i] | | X | X | X | X | | | | | X[j] |
| Infant skin monitoring (e.g., AD, skin rash, diaper rash, itch)[k] | | X | X | X | X | X | X | X | X | X |
| Interview Caregivers and (as applicable) review medical records for: | | | | | | | | | | |
| Infant AEs | | X | X | X | X | X | X | X | X | X |
| Concurrent product use | | X | X | X | X | X | X | X | X | X |
| Signs of atopic disease other than AD[l] (asthma, allergic rhinitis, food allergy) | | X | X | X | X | X | X | X | X | X |

TABLE 5-continued

Schedule of Events

| Study Period | Screening | Supplementation Period | | | | Follow-up Period | | | |
| --- | --- | --- | --- | --- | --- | --- | --- | --- | --- |
| Study Visit[a, b] Additional definitions | Within 14 days postpartum[c] | Day 0 Baseline[d] | Week 6 | Week 12 (~3 months) EOS | Week 24 | Week 52 (~1 year) | Week 76 | Week 104 (~2 years) | Early D/C D/C[e] | Unscheduled Study Visit |
| Signs and symptoms of infantile colic (based on Rome IV criteria) | | X | X | X | X | | | | X[m] | |
| Infant routines and care (e.g., daycare, bowel movements, updated allergen exposures) | | X | X | X | X | X | X | X | X | |
| POEM (only for infants with AD) | | At time of AD diagnosis and at Weeks 12, 52, and 104 | | | | | | | X | X[n] |
| EASI (only for infants with AD) | | At time of AD diagnosis and at Weeks 12, 52, and 104 | | | | | | | X | X[n] |
| Infant anthropometrics[o] | | X | X | X | X | X | X | X | X | X |
| Data Collected via eDiary[p] | | | | | | | | | | |
| Infant Feeding and Study Supplement Usage Log | | | Daily | | | Optional completion of feeding log | | | | |
| Infantile colic (e.g., crying/fussiness; based on Rome IV criteria) | | X | X Weeks 5-7 | X Weeks 11-13 | X Week 23-24 | | | | | |
| BISQ-R | | | | X | X | X | X | | | |
| Solid Food Introduction Checklist | | | Complete when new food introduced (one time per food) | | | | | | | |
| Biological Sample Collection | | | | | | | | | | |
| Blood samples: | | | | | | | | | | |
| 2.0 mL venous sample | | | | | X[q] | X[q] | | X[q] | X[r] | |
| Stool samples: | | | | | | | | | | |
| Infant gut microbiome (including *B. infantis* gut colonization)[s] | | X | X | X | X | X | | X | X[r] | |
| Maternal gut microbiome[s, t] | | | | X | | | | | | |
| Skin samples (swabs): | | | | | | | | | | |
| Biomarker profile (FibroTX kit) | | X[u] | | X[u] | | X[u] | | | X[r, u] | |
| Microbiome | | X[u] | X[u] | X[u] | | X[u] | | | X[r, u] | |

Study Endpoints and Data Analysis

Primary Endpoint: Cumulative Incidence of AD through Week 52. The cumulative incidence of AD through Week 52 will be compared between supplementation groups.

Secondary Endpoints:
  Distributions for time to onset of AD through Week 104 will be compared between supplementation groups
  Cumulative incidence of AD through Weeks 24 and 104
  Proportion of Infants with *B. infantis* Gut Colonization at Week 12: Week 12 stool samples will be analyzed for *B. infantis* colonization and for the overall bacterium load to determine the proportion of infants with *B. infantis* gut colonization. An infant's gut will be considered colonized as defined above.
  AD severity based on the EASI score at time of AD onset and at Weeks 12, 52, and 104
  AD severity based on the POEM score at time of AD onset and at Weeks 12, 52, and 104

Additional Endpoints:
  Cumulative Incidences of Atopic Disease Other than AD through Weeks 24, 52, and 104: Study Personnel will document the development of allergic rhinitis, asthma, and food allergy (as confirmed by a specialist/pediatric allergist) throughout the study, and cumulative incidences of these disorders will be determined at Weeks 24, 52, and 104.
  Cumulative Incidence of Allergic Sensitization through Weeks 24, 52, and 104: Study Personnel will document the development of allergic sensitization such as against dietary or inhaled allergens (as confirmed by specific serum IgE testing), and cumulative incidences will be determined at Weeks 24, 52, and 104.
  Changes from Baseline in Gut and Skin Microbiome through Week 104: Changes from baseline in fecal (Weeks 6, 12, 24, 52, and 104) and skin (Weeks 6, 12, and 52) microbiome will be determined.
  Proportion of Infants with *B. infantis* Gut Colonization at Week 24: Stool samples collected in association with the Week 24 visit will be analyzed for *B. infantis* gut colonization as detailed above.
  Changes from Baseline in Skin Immunological Biomarker Profile at Weeks 12 and 52: Changes from baseline in skin biomarkers at Weeks 12 and 52 will be determined.
  Cumulative Incidence of Infantile Colic through Weeks 6, 12, and 24: A diagnosis of infantile colic will be based on the Rome IV criteria, which include data generated by visit interviews and Caregiver diary.

BISQ-R Scores at Weeks 12, 24, 52, and 76: BISQ-R infant sleep, parent perceptions, and parent behavior subscale scores, as well as the total BISQ-R score at Weeks 12, 24, 52, and 76 will be determined.

Changes from Baseline in Infant Anthropometrics at Weeks 6, 12, 24, 52, 76, and 104: Changes from baseline in infant's length/height, body weight, head circumference, and BMI at Weeks 6, 12, 24, 52, 76, and 104 will be determined.

Influence of Maternal Gut Microbiome on Infant Gut Microbiome Development from Baseline to Two Years of Age: The microbiome of maternal stool samples collected 2-6 weeks postpartum will be assessed for correlations with development of the infant gut microbiome, including infant *B. infantis* gut colonization, at Baseline (Day 0) and Weeks 6, 12, 24, 52, and 104.

Microbiome and Immunological Profiles in Infants With or Without AD: Outcomes measures relating to microbiome and immunological profiles will be characterized in and compared between infants who do not develop AD through 1 year and infants who do in the *B. infantis* (EVC001) supplementation group and in the placebo supplementation group.

Serial RNA Expression Analysis at Weeks 24, 52, and 104: Outcome measures relating to serial RNA expression profiles will be characterized in and compared between subjects in the *B. infantis* (EVC001) supplementation group and in the placebo supplementation group at Weeks 24, 52, and 104 to investigate the infant immune responder phenotype.

Subject Genetic Analysis: Outcome measures relating to subject genetic profiles will be characterized in and compared between infants who do not develop AD through 1 year and infants who do in the *B. infantis* (EVC001) supplementation group to identify subjects who are likely to benefit from the intervention.

Success Criteria

The success of the study will primarily be determined by a statistically significant effect of supplementation versus placebo on the cumulative incidence of AD through Week 52.

Summary

The above example constitutes a method comprising administering a composition comprising a *Bifidobacterium* (*B. infantis*) to a breastfed infant having an increased risk of developing an atopic disease. Atopic dermatitis, food allergy, allergic rhinitis and asthma will be monitored and evaluated for indications of prevention, delay and/or amelioration in the breastfed infants. Infantile colic, infant sleep and infant anthropometrics will also be monitored and evaluated.

Example 3: LEAP (Learning Early About Peanut) and LEAP-On (Follow-on Study) Trials: Clinical Trials Investigating How to Best Prevent Peanut Allergy These clinical trials investigate how early introduction and regular consumption of peanut in infants at high risk for food allergy prevents peanut allergy, and likely induces durable, and long-lasting tolerance (see, e.g., www.leap-study.co.uk; Elissa M. Abrams, et al., "International Peanut Allergy prevention, 6 Years After the Learning Early About Peanut Study," J. Allergy Clin. Immunol Pract., January 2022, Volume 10 (1): 71-77; and George Du Toit, et al., "Randomized Trial of Peanut Consumption in Infants at Risk for Peanut Allergy," N. Engl. J. Med., February 2015, Volume 372 (9): 803-813).

Objectives

How long-lasting is the impact of early childhood exposure to peanut.
Whether this therapy impacted siblings' risk of developing peanut allergy.
Whether parental characteristics impact the development of peanut allergy.

Results

Among the 530 infants in the intention-to-treat population who initially had negative results on the skin-prick test, the prevalence of peanut allergy at 60 months of age was 13.7% in the avoidance group and 1.9% in the consumption group (P<0.001). Among the 98 participants in the intention-to-treat population who initially had positive test results, the prevalence of peanut allergy was 35.3% in the avoidance group and 10.6% in the consumption group (P=0.004). There was no significant between-group difference in the incidence of serious adverse events. Increases in levels of peanut-specific IgG4 antibody occurred predominantly in the consumption group; a greater percentage of participants in the avoidance group had elevated titers of peanut-specific IgE antibody. A larger wheal on the skin-prick test and a lower ratio of peanut-specific IgG4: IgE were associated with peanut allergy.

Example 4: EAT (Enquiring About Tolerance) Trial: Feasibility of an Early Allergenic Food Introduction Regimen The Enquiring About Tolerance (EAT) study was to test the hypothesis that the early introduction of multiple allergenic foods from 3 months of age in an unselected population of exclusively breastfed infants will, as a primary outcome, reduce the prevalence of food allergy and, as a secondary outcome, influence asthma, eczema, allergic rhinitis, and the prevalence of combined allergic disease by 3 years of age. (see, e.g., www.ncbi.nlm.nih.gov/pmc/articles/PMC4852987; and Michael R. Perkin, et al., "Randomized Trial of Introduction of Allergenic Foods in Breast-Fed Infants," N. Engl. J. Med., 2016, 374: 1733-1743).

Objectives

To determine the feasibility of the early introduction of multiple allergenic foods to exclusively breast-fed infants from 3 months of age and the effect on breastfeeding performance.

Results

One thousand three hundred three infants were enrolled. By 5 months of age, the median frequency of consumption of all 6 foods was 2 to 3 times per week for every food in the EIG and no consumption for every food in the standard introduction group (P<0.001 for every comparison). By 6 months of age, nonintroduction of the allergenic foods in the EIG was less than 5% for each of the 6 foods. Achievement of the stringent per-protocol consumption target for the EIG proved more difficult (42% of evaluable EIG participants). Breastfeeding rates in both groups significantly exceeded UK government data for equivalent mothers (P<0.001 at 6 and at 9 months of age).

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

The invention claimed is:

1. A method of immune system regulation in an infant, comprising:
   identifying an infant at high risk for atopic dermatitis based on at least a parental history of atopic disease;
   administering to the infant a composition comprising about 5 billion to about 15 billion colony-forming units (CFU) of *Bifidobacterium infantis* (*B. infantis*) once daily for at least 12 weeks, wherein the administration starts within about 30 days of birth;
   treating the skin of the infant with an effective amount of an emollient, comprising:
      about 0.005% to about 0.1% ceramide 3, and
      saturated fatty acids,
      wherein the ceramide and saturated fatty acids creates a water-impermeable, protective layer to prevent excessive water loss due to evaporation and provide a barrier against the entry of microorganisms,
   at least once a day for at least 8 weeks, wherein the treating begins within about 4 days of birth; and
   orally administering to the infant a premeasured dose of one to six allergenic foods within about 1-8 months after the birth of the infant;
   wherein the method provides a statistically significant reduction in atopic dermatitis at 12 months or at 52 weeks compared to an untreated group in a clinical setting.

2. The method of claim 1, wherein the composition comprises about 8 billion CFU of *B. infantis*.

3. The method of claim 1, wherein the *B. infantis* composition is administered as a mixture with breast milk.

4. The method of claim 1, wherein the *B. infantis* composition is administered as a mixture with infant formula.

5. The method of claim 1, wherein the allergenic foods are include at least one of cow milk, egg, peanut, wheat, soy, sesame, fish, shellfish, or and tree nut.

6. The method of claim 1, wherein the method provides a 50% reduction of atopic dermatitis at 6 months.

7. The method of claim 1, wherein the method provides a 29% reduction of atopic dermatitis at 12 months.

8. The method of claim 1, wherein the emollient comprises:
   a. less than about 1.0% caprylic/capric triglyceridem
   b. less than about 0.1% citric acid,
   c. less than about 2.0%; benzoic acid,
   d. less than about 2.0% potassium phosphate,
   e. less than about 10.0% dimethicone,
   f. less than about 2.0% palmitic acid,
   g. less than about 10% isocetyl alcohol,
   h. less than about 2.0% *Avena sativa* (oat) kernel flour,
   i. less than about 2.0% ethylhexylglycerin,
   j. less than about 1.0% *Avena sativa* (oat) kernel oil,
   k. less than about 1.0% *Avena sativa* (oat) kernel extract,
   l. Less than about 40% water,
   m. less than about 50% glycerin,
   n. less than about 2.0% sodium cetearyl sulfate,
   o. less than about 2.0% dipotassium phosphate,
   p. less than about 1.0% sodium hydroxide,
   q. less than about 10.0% cetyl alcohol,
   r. less than about 10.0% cetearyl alcohol,
   S. less than about 2.0% benzyl alcohol, and
   t. less than about 2.0% p-anisic acid.

9. The method of claim 8, wherein the emollient comprises:
   a. at least about 0.005% caprylic/capric triglyceride;
   b. at least about 0.005 citric acid;
   c. at least about 0.1% benzoic acid,
   d. at least about 0.05% potassium phosphate,
   e. at least about 1.0% dimethicone,
   f. at least about 0.1% palmitic acid,
   g. at least about 1.0% isocetyl alcohol,
   h. at least about 0.1% *Avena sativa* (oat) kernel flour,
   i. at least about 0.1% ethylhexylglycerin,
   j. at least about 0.005% *Avena sativa* (oat) kernel oil,
   k. at least about 0.005% *Avena sativa* (oat) kernel extract,
   l. At least about 15.0% water,
   m. at least about 20.0% glycerin,
   n. at least about 0.1% sodium cetearyl sulfate,
   o. at least about 0.1% dipotassium phosphate,
   p. at least about 0.005% sodium hydroxide,
   q. at least about 1.0% cetyl alcohol,
   r. at least about 1.0% cetearyl alcohol,
   s. at least about 0.1% benzyl alcohol, and
   t. at least about 0.1% p-anisic acid.

10. The method of claim 9, wherein, in the emollient,
   i. caprylic/capric triglyceride creates a barrier on the skin's surface, which helps to reduce skin dryness by decreasing the loss of moisture;
   ii. dimethicone acts as a skin protectant;
   iii. stearic acid and palmitic acid create an occlusive barrier that protects skin from unwanted microbes and pollutants while retaining moisture; and
   iv. glycerin hydrates the outer layer of the skin and improves skin barrier function and skin mechanical properties.

11. The method of claim 1, wherein the *B. infantis* is strain EVC001.

12. The method of claim 1, further comprising co-administering with the *B. infantis* one or more probiotics different from *B. infantis*.

13. The method of claim 12, wherein the one or more probiotics is selected from *Lactiplantibacillus plantarum*, *Limosilactobacillus fermentum*, and *Ligilactobacillus salivarius*.

14. The method of claim 1, further comprising monitoring stool samples of the infant to determine colonization of *B. infantis*.

15. The method of claim 1, wherein the premeasured dose is between about 0.01 and 0.3 grams.

16. The method of claim 1, further comprising administering a maintenance dose of each allergenic food.

17. The method of claim 16, wherein the maintenance dose of each food allergen is between about 0.05 and 1 grams.

18. The method of claim 1, wherein the treating of the skin of the infant is before the administering to the infant the *B. infantis*.

19. The method of claim 1, wherein the treating of the skin of the infant is after the administering to the infant the *B. infantis*.

20. The method of claim 1, wherein the emollient comprises colloidal oatmeal and distearyldimonium chloride.

* * * * *